US012778933B2

(12) United States Patent
Gurkan et al.

(10) Patent No.: US 12,778,933 B2
(45) **Date of Patent: *Nov. 3, 2026**

(54) TREATMENT OF GLAUCOMA USING ENDOTHELIN RECEPTOR ANTAGONISTS

(71) Applicant: Perfuse Therapeutics, Inc., San Francisco, CA (US)

(72) Inventors: Sevgi Gurkan, Belmont, CA (US); David Floyd, Pennington, NJ (US)

(73) Assignee: Perfuse Therapeutics, Inc., South San Francisco, CA (US)

( * ) Notice: Subject to any disclaimer, the term of this patent is extended or adjusted under 35 U.S.C. 154(b) by 474 days.

This patent is subject to a terminal disclaimer.

(21) Appl. No.: 18/345,514

(22) Filed: Jun. 30, 2023

(65) Prior Publication Data

US 2024/0189288 A1 Jun. 13, 2024

Related U.S. Application Data

(63) Continuation of application No. 17/733,216, filed on Apr. 29, 2022, now Pat. No. 11,738,007, which is a continuation of application No. PCT/US2020/058411, filed on Oct. 30, 2020.

(60) Provisional application No. 63/068,215, filed on Aug. 20, 2020, provisional application No. 62/928,092, filed on Oct. 30, 2019.

(51) Int. Cl.

| | |
|---|---|
| ***A61K 31/422*** | (2006.01) |
| ***A61K 9/00*** | (2006.01) |
| ***A61K 9/08*** | (2006.01) |
| ***A61K 9/10*** | (2006.01) |
| ***A61K 9/19*** | (2006.01) |
| ***A61K 31/36*** | (2006.01) |
| ***A61K 31/4025*** | (2006.01) |
| ***A61K 47/10*** | (2017.01) |
| ***A61K 47/18*** | (2017.01) |
| ***A61K 47/22*** | (2006.01) |
| ***A61K 47/40*** | (2006.01) |
| ***A61P 27/02*** | (2006.01) |
| ***A61P 27/06*** | (2006.01) |

(52) U.S. Cl.

CPC .......... *A61K 31/422* (2013.01); *A61K 9/0014* (2013.01); *A61K 9/0019* (2013.01); *A61K 9/0048* (2013.01); *A61K 9/0051* (2013.01); *A61K 9/08* (2013.01); *A61K 9/10* (2013.01); *A61K 9/19* (2013.01); *A61K 31/36* (2013.01); *A61K 31/4025* (2013.01); *A61K 47/10* (2013.01); *A61K 47/18* (2013.01); *A61K 47/22* (2013.01); *A61K 47/40* (2013.01); *A61P 27/02* (2018.01); *A61P 27/06* (2018.01)

(58) Field of Classification Search

None

See application file for complete search history.

(56) References Cited

U.S. PATENT DOCUMENTS

| | | | | |
|---|---|---|---|---|
| 5,364,374 | A * | 11/1994 | Morrison ............ | A61F 9/00781 604/521 |
| 6,043,265 | A | 3/2000 | Murugesan et al. | |
| 7,927,613 | B2 | 4/2011 | Almarsson et al. | |
| 8,980,874 | B2 | 3/2015 | Gulati | |
| 9,610,246 | B2 | 4/2017 | Shiah et al. | |
| 2003/0176356 | A1 * | 9/2003 | Yorio .................. | A61K 9/0019 514/16.1 |
| 2004/0063731 | A1 * | 4/2004 | Eggenweiler ........... | A61P 11/02 514/262.1 |
| 2004/0234611 | A1 | 11/2004 | Ahlheim et al. | |
| 2007/0116729 | A1 | 5/2007 | Palepu | |
| 2007/0260203 | A1 | 11/2007 | Donello et al. | |
| 2009/0054473 | A1 | 2/2009 | Roden et al. | |
| 2011/0275715 | A1 | 11/2011 | Mashima et al. | |
| 2015/0118279 | A1 | 4/2015 | Ghebremeskel et al. | |
| 2016/0331712 | A1 | 11/2016 | Georgiou | |
| 2016/0346224 | A1 | 12/2016 | Macdonald | |
| 2018/0110728 | A1 | 4/2018 | Duran Muiños et al. | |
| 2018/0362570 | A1 | 12/2018 | Ganapati et al. | |
| 2019/0015521 | A1 | 1/2019 | Roizman | |
| 2020/0230157 | A1 | 7/2020 | Williams et al. | |
| 2020/0306182 | A1 | 10/2020 | Das et al. | |

(Continued)

FOREIGN PATENT DOCUMENTS

| | | | |
|---|---|---|---|
| JP | H 9-59173 | A | 3/1997 |
| WO | WO-2002/032884 | A2 | 4/2002 |

(Continued)

OTHER PUBLICATIONS

Shoshani, Yochai Z., et al. "Endothelin and its suspected role in the pathogenesis and possible treatment of glaucoma." Current eye research 37.1 (2012): 1-11. (Year: 2012).*

Davenport, Anthony P., et al. "Endothelin." Pharmacological reviews 68.2 (2016): 357-418. (Year: 2016).*

Davenport, et al., "Endothelin." Pharmacological reviews (2016) 68:357-418.

Francesco Boscia, "Current Approaches to the Management of Diabetic Retinopathy and Diabetic Macular Oedema", 70 Drugs 2171 (Year: 2010).

Hulpke-Wette, et al., "BMS-193884 and BMS-207940 Bristol-Myers Squibb" Current Opinion in Investigational Drugs (2002), 3(7), 1057-1061.

International Search Report and Written Opinion mailed Feb. 3, 2021, for International Application No. PCT/US2020/058411 filed Oct. 30, 2020. (8 pages).

(Continued)

*Primary Examiner* — Bethany P Barham
*Assistant Examiner* — Peter Anthopolos
(74) *Attorney, Agent, or Firm* — Goodwin Procter LLP

(57) ABSTRACT

The present disclosure relates to the discovery that certain diseases of the eye that profoundly affect the human visual system and, as a result, quality of life, may be treated using Edonentan or A-182086. Edonentan or A-182086 can be used alone or in combination with an intra-ocular pressure (IOP) reducing agent, a neuroprotective agent, an anti-VEGF agent, or all, for example. Using Edonentan or A-182086, alone or in combination with an additional agent, provides increased perfusion to the retina in certain diseases and reduces damage to retinal cells.

21 Claims, 28 Drawing Sheets

(56) References Cited

U.S. PATENT DOCUMENTS

2022/0257505 A1 8/2022 Gurkan et al.
2022/0257568 A1 8/2022 Gurkan et al.

FOREIGN PATENT DOCUMENTS

WO WO-2010/144477 A2 12/2010
WO WO-2016/156639 A1 10/2016
WO WO-2017/217967 A1 12/2017
WO WO-2018/185516 A1 10/2018
WO WO-2019/210194 A1 10/2019
WO WO-2021/087399 A1 5/2021
WO WO-2021/158663 A1 8/2021
WO WO-2022/232588 A1 11/2022

OTHER PUBLICATIONS

International Search Report and Written Opinion mailed Sep. 14, 2022, for International Application No. PCT/US2022/27048 filed Apr. 29, 2022. (12 pages).
International Search Report of International Application No. PCT/US2021/016414 mailed Apr. 15, 2021, 4 pages.
PUBCHEM-SID:376333874 Deposit Date: Nov. 30, 2018 (Nov. 30, 2018) pp. 1-6; p. 2.
Rosenthal Rita et al., "Endothelin Antagonism as an Active Principle for Glaucoma Therapy." British Journal of Pharmacology (2011) 162, 806-816.
Sasaoka et al., "Intravitreal injection of endothelin-1 caused optic nerve damage following to ocular hypoperfusion in rabbits" Experimental Eye Research 83 (2006) 629-637.
Shoshani, et al., "Endothelin and its suspected role in the pathogenesis and possible treatment of glaucoma" Current Eye Research 37(1), 1-11, 2012.
Anna-Leena Siren, et al., Endothelin B Receptor Deficiency Augments Neuronal Damage Upon Exposure to Hypoxia-Ischemia In Vivo, 945 Brain Res. 144 (Year:2002) (library ref).
Goto et al. "Molecular Pharmacology and Pathophysiological Significance of Endothelin" Jpn. J. Pharmacol. 72, 261-290 (1996).
J.W. Kiel "Endothelin Modulation of Choroidal Blood Flow in the Rabbit" Exp Eye Res. 2000, 71(6), pp. 543-550.
Li et al. "Endothelin and Diabetic Complications: a Brain-Centric View" Physiol. Res. 67 (Suppl. 1): S83-S94, 2018.
Maturi et al. "Four-Year Visual Outcomes in the Protocol W Randomized Trial of Intravitreous Aflibercept for Prevention of Vision-Threatening Complications of Diabetic Retinopathy" JAMA. 2023; 329(5): 376-385.
Miglior et al (Current Opinion in Pharmacology, 2013; 13:32-35) (Year: 2013).
Prasanna et al. "Endothelin, Astrocytes and Glaucoma" Exp Eye Res. Aug. 2011, 93(2), pp. 170-177.
Sidney G. Shaw, et al., "Edonentan Antagonism Prevents Diabetic Retinopahy in NOD Mice: A Potential Role fo the Angiogenic Factor Adrenomedullin," 231 Exp. Bio. Med. 1101 (2006)).
Sun et al. "Mitophagy protects the retina against anti-vascular endothelial growth factor therapy-driven hypoxia via hypoxia-inducible fact-1 alpha signaling" Front. Cell. Dev. Biol. 9:727822.
Takagi et al. "Regulation of Retinal Hemodynamics in Diabetic Rats by Increased Expression and Action of Endothelin-1" Investigative Ophthalmology & Visual Science, 1996, 37, 2504-2518.
Vecino et al. "Glaucoma Animal Models" Glaucoma—Basic and Clinical Concepts; www.intecho <http://www.intechopen.com; pp. 319-335.
Veurink et al. "Development of an Intravitreal Peptide (BQ123) Sustained Release System Based on Poly(2-Hydroxyoctanoic Acid) Aiming at a Retinal Vasodilator Response" Journal of Ocular Pharmacolo and Therapeutics, 2014, 30, pp. 517-523.
Wang and Lo "Diabetic Retinopathy: Pathophysiology and Treatments" Int. J. Mol. Sci., 2018, 19, 1816: do: 10.3390/ijms1906816.
Wykoff et al. "Retinal non-perfusion in diabetic retinopathy" Nature, Eye, 2022, 36:249-256.
Polak et al. "Effect of Endothelin and BQ123 on Ocular Blood Flow Parameters in Healthy Subjects" Investigative Ophthalmolo & Visual Science, 2001, 42, 2949-2956.
Prasanna et al. "Effect of elevated intraocular pressure on endothelin-1 in a rat model of glaucoma" Pharmacological Research 51 (2005) pp. 41-50.
Allison, K et al. "Epidemiology of Glaucoma: The Past, Present, and Predictions for the Future" Cureus 12(11): Nov. 24, 2020.
Urtii, A. "Challenges and obstacles of ocular pharmacokinetics and drug delivery" Advanced Drug Delivery Reviews 58 (2006) 1131-1135.
Murugesan et al., "Biphenylsulfonamide Endothelin receptor Antagonists", Journal of Medicinal Chemistry, American Chemical Society, US, vol. 46, No. 1, Nov. 26, 2002, pp. 135-137.
Caira et al., "Crystalline Polymorphism of Organic Compounds", Topics in Current Chemistry; Spring Berlin, DE, vol. 198, Jan. 1, 1998, pp. 163-208.
Teo ZL, et al. "Global Prevalence of Diabetic Retinopathy and Projection of Burden through 2045: Systematic Review and Meta-analysis." Ophthalmology. Nov. 2021; 128(11):1580-1591. doi: 10.1016/j.ophtha.2021.04.027. Epub May 1, 2021.
Simó R., et al. "Neurodegeneration in diabetic retinopathy: does it really matter?" Diabetologia. Sep. 2018;61(9):1902-1912. doi: 10.1007/s00125-018-4692-1. Epub Jul. 20, 2018.
Kim CB, et al. "Revisiting the mouse model of oxygen-induced retinopathy." Eye Brain. 2016;8:67-79. doi: 10.2147/EB.S94447. Epub May 20, 2016.
Bogdanov P. et al. "Topical Administration of Bosentan Prevents Retinal Neurodegeneration in Experimental Diabetes." Int J Mol Sci. Nov. 13, 2018;19(11):3578. doi: 10.3390/ijms19113578.
Alrashdi SF et al. "Intravitreal administration of endothelin type A receptor or endothelin type B receptor antagonists attenuates hypertensive and diabetic retinopathy in rats." Exp Eye Res. Nov. 2018;176:1-9. doi: 10.1016/j.exer.2018.06.025. Epub Jun. 23, 2018.
Bresnick GH et al. "Retinal ischemia in diabetic retinopathy." Arch Ophthalmol. Dec. 1975;93(12):1300-10. doi: 10.1001/archopht.1975.01010020934002.
Nicholson L et al. "Mechanistic Evaluation of Panretinal Photocoagulation Versus Aflibercept in Proliferative Diabetic Retinopathy: CLARITY Substudy." Invest Ophthalmol Vis Sci. Aug. 1, 2018;59(10):4277-4284. doi: 10.1167/iovs.17-23509.
Yorio et al. "Endothelin: is it a contributor to glaucoma pathophysiology" Journal of Glaucoma 11.3, 259-270. (2002).
Howell GR, et al. "Combinatorial targeting of early pathways profoundly inhibits neurodegeneration in a mouse model of glaucoma." Neurobiol Dis. Nov. 2014;71:44-52.
Howell GR, et al. "Molecular clustering identifies complement and endothelin induction as early events in a mouse model of glaucoma." J Clin Invest. Apr. 2011;121(4):1429-44.
Rosenthal R, et a. "Endothelin antagonism as an active principle for glaucoma therapy." Br J Pharmacol. Feb. 2011;162(4):806-16.
Speicher et al, Pharmacologic therapy for diabetic retinopathy, Expert Opinion on Emerging Drugs, 8:1, pp. 239-250, 2003.
Kern et al., Pharmacological Inhibition of Diabetic Retinopathy Aminoguanidine and Aspirin, Diabetes, vol. 50, Jul. 2001.
Comer et al., Current and future pharmacological intervention for diabetic retinopathy, Expert Opinion on Emerging Drugs, 10(2), pp. 441-455 (2005).
Villegas et al., Current and Future Pharmacologic Therapies for Diabetic Retinopathy, Current Pharmaceutical Design, 24, pp. 4903-4910, (2018).
Konno T et al: "Effect of chymase on intraocular pressure in rabbits," European Journal Of Pharmacology; 524 (2005) pp. 132-137.

* cited by examiner

CTRL: Vehicle control
*$p < 0.05$ n = 10 mice/group

** p < 0.002
N=4 rats/group (Vehicle)
N=6 rats/group (Edonentan)

** p < 0.03
N=4 rats/group (Vehicle)
N=5 rats/group (Edonentan)

** p < 0.008
N=4 rats/group (Vehicle)
N=6 rats/group (A-182086)

* p < 0.04
N=4 rats/group (Vehicle)
N=5 rats/group (A-182086)

EG: Experimental Glaucoma Eye, Control: Contralateral Healthy Eye

EG: Experimental Glaucoma Eye, Control: Contralateral Healthy Eye

EG: Experimental Glaucoma Eye, Control: Contralateral Healthy Eye

EG: Experimental Glaucoma Eye, Control: Contralateral Healthy Eye

EG: Experimental Glaucoma Eye, Control: Contralateral Healthy Eye

EG: Experimental Glaucoma Eye, Control: Contralateral Healthy Eye

EG: Experimental Glaucoma Eye, Control: Contralateral Healthy Eye

EG: Experimental Glaucoma Eye, Control: Contralateral Healthy Eye

EG: Experimental Glaucoma Eye, Control: Contralateral Healthy Eye

EG: Experimental Glaucoma Eye, Control: Contralateral Healthy Eye

EG: Experimental Glaucoma Eye, Control: Contralateral Healthy Eye

EG: Experimental Glaucoma Eye, Control: Contralateral Healthy Eye

TREATMENT OF GLAUCOMA USING ENDOTHELIN RECEPTOR ANTAGONISTS

RELATED APPLICATIONS

This application is a continuation of U.S. Non-provisional patent application Ser. No. 17/733,216 filed on Apr. 29, 2022, which is a continuation of International Application Number PCT/US2020/058411 filed on Oct. 30, 2020, which claims priority to U.S. Provisional Patent Application Nos. 62/928,092 and 63/068,215, respectively filed on Oct. 30, 2019 and Aug. 20, 2020; the entire contents of each of which are hereby incorporated by reference for all purposes.

FIELD

The present disclosure relates to the field of medicine and the treatment of ocular disease. More specifically, the present disclosure relates to the use of Edonentan and A-182086 endothelin receptor antagonists in the treatment or amelioration of glaucoma, diabetic retinopathy (DR), retinal vein occlusion (RVO), non-arteritic anterior ischemic optic neuropathy (NAION), arteritic anterior ischemic optic neuropathy (AION), and retinopathy of prematurity (ROP).

BACKGROUND

Diseases of the eye have an enormous impact on the quality of human life and yet remain largely elusive to effective treatment. It is estimated that an annual economic burden of over $100 billion results from vision loss, eye diseases, and vision disorders in the U.S. Examples of debilitating ocular diseases include glaucoma, diabetic retinopathy (DR), retinal vein occlusion (RVO), non-arteritic anterior ischemic optic neuropathy (NAION), arteritic anterior ischemic optic neuropathy (AION), and retinopathy of prematurity (ROP).

Glaucoma is an eye disorder characterized by visual field defects and excavation of the optic nerve head. An abnormally high intraocular pressure is commonly known to be detrimental to the eye, and there are clear indications that, in glaucoma patients, this probably is the most important physical change causing degeneration of the retina. Ultimately, if untreated, there is gradual loss of vision over time. The pathophysiological mechanism of glaucoma is, however, still unknown.

There are three basic types of glaucoma: primary, secondary, and congenital. Primary glaucoma is the most common type and can be divided into open-angle and closed-angle glaucoma. Primary open angle glaucoma ("POAG") is the most frequent type of glaucoma observed in the United States. POAG is usually detected in its early stages during routine eye examinations. Primary closed angle glaucoma, also called acute glaucoma, usually has a sudden onset and is characterized by eye pain and blurred vision. Secondary glaucoma occurs as a complication of a variety of other conditions, such as injury, inflammation, generalized vascular disease, and diabetes. Congenital glaucoma is due to a developmental defect in the eye's drainage mechanism.

Diabetic retinopathy (DR) is the most common complication of diabetes and the leading cause of decreased visual acuity and blindness in working-age population in developed countries. The incidence of DR increases with the time of evolution of diabetes. Thus, 90% of patients with type 1 diabetes and 60% of patients with type 2 diabetes have some degree of DR after 20 years of evolution of diabetes. The prevalence of DR in Western countries is very similar and is around 30% and in 10% of cases the DR is in advanced stages that seriously threaten vision.

DR occurs when changes in blood glucose levels cause changes in retinal blood vessels. In some cases, these vessels will swell up (macular edema) and leak fluid into the rear of the eye. In other cases, abnormal blood vessels will grow on the surface of the retina. Unless treated, DR can gradually become more serious and progress from 'background retinopathy' to seriously affecting vision and can lead to blindness.

Retinal vein occlusion (RVO) is a vascular disorder of the retina and one of the most common causes of vision loss worldwide. Specifically, it is the second most common cause of blindness from retinal vascular disease after diabetic retinopathy. RVO is often the result of underlying health problems (e.g., high blood pressure, high cholesterol levels, diabetes, and other health problems). There are two types of retinal vein occlusion: central retinal vein occlusion (CRVO) is the blockage of the main retinal vein, and branch retinal vein occlusion (BRVO) is the blockage of one of the smaller branch veins.

Currently, there is no way to unblock retinal veins, and accepted treatments are directed to addressing health problems related to the retinal vein occlusion. Vision may come back in some eyes that have had a retinal vein occlusion. About ⅓ have some improvement, about ⅓ stay the same and about ⅓ gradually improve, but it can take a year or more to determine the final outcome. In some cases, the blocked vessels will lead to fluid accumulation in the retina. In other cases, occurrence of ischemia causes the formation of new blood vessels. RVO is currently treated with intravitreal injection of anti-vascular endothelial growth factor (VEGF) drugs.

Anterior ischemic optic neuropathy (AION) results from ischemic damage to the anterior portion of the optic nerve, a region primarily supplied by the posterior ciliary artery circulation. Anterior ischemic optic neuropathy is divided into two types: arteritic AION (AAION), secondary to vasculitis (especially giant cell arteritis), and nonarteritic AION (NAION), secondary to non-inflammatory small vessel disease. NAION constitutes 95% of all AION and is the most common cause of acute optic neuropathy in people over the age of 50, affecting somewhere between 2 to 10 individuals per 100,000 (approximately 1500 to 6000 new cases per year in the United States). Currently, no generally accepted treatment or secondary prevention of NAION exists, however steroids have been traditionally used in some patients.

Retinopathy of prematurity (ROP) can occur due to premature birth. Abnormal, leaky blood vessel growth (neovascularization) in the retina occurs secondary to other treatments for prematurity and can often lead to neonatal blindness. During pregnancy, blood vessels grow from the center of a developing baby's retina 16 weeks into the mother's pregnancy, and then branch outward and reach the edges of the retina 8 months into the pregnancy. In babies born prematurely, normal retinal vessel growth is incomplete and may therefore be more readily disrupted.

Edonentan is a highly selective and very potent endothelin A receptor antagonist. Edonentan was developed as a second-generation analog following the discontinuation of the first clinical candidate, BMS-193884, which was being developed for the treatment of congestive heart failure (CHF). Edonentan was in phase I trials by April 2002, but its development was discontinued.

A-182086 is a potent dual $ET_A/ET_B$ receptor antagonist with 4-fold $ET_A/ET_B$ selectivity. A-182086 has not been studied in a clinical setting to date.

There remains a need to more effectively reduce the incidence of, treat or otherwise ameliorate glaucoma, DR, RVO, NAION, AION, and ROP.

SUMMARY

The present invention provides a method of using the endothelin receptor antagonists for treating an ocular disease selected from glaucoma, diabetic retinopathy (DR), retinal vein occlusion (RVO), non-arteritic anterior ischemic optic neuropathy (NAION), arteritic anterior ischemic optic neuropathy (AION), and retinopathy of prematurity (ROP).

The method comprises contacting an optical tissue in a subject with a composition comprising a therapeutically effective amount of Edonentan or A-182086, or a pharmaceutically acceptable salt thereof, in which the endothelin receptor antagonist is Edonentan or A-182086. Such antagonist or its pharmaceutically acceptable salt can be in a crystalline form or an amorphous form, each of which can be for pharmacologically acceptable use.

In some embodiments, contacting comprises administering a topical composition to a surface of an eye or a portion thereof. In other embodiments, contacting comprises injecting Edonentan or A-182086 into an eye generally or in a specific area thereof.

In still other embodiments, contacting comprises administering a composition via an eye implant, e.g., a port delivery system. Examples of eye implant technologies include, but are not limited to, ApidCOR, BioSeizer-ProDex, Vitrasert, Retisert, Iluvien, I-Vation, Nanoporous Silicon, Ozurdex/Novadur, OcuLief, Port Delivery System (PDS), PEA Implant, PEG-PLA Microspheres, PRINT Technology, Q-Sphera, SKS Microparticles, Verisome, Capsule Ring Device, MicroPump, Microneedle Injector, Microneedle/Needle-less Injectors, EyeCET, Gemini Refractive Capsule, IVMED, Ciliary Sulcus Ring, Episcleral Exoplant, Eye-D Implant, and Nanoliposomes.

In some embodiments, the eye implant technologies that can be used in the methods of this disclosure is selected from ApidCOR, BioSeizer-ProDex, Vitrasert, Retisert, Iluvien, I-Vation, Nanoporous Silicon, Ozurdex/Novadur, OcuLief, Port Delivery System (PDS), PEA Implant, PEG-PLA Microspheres, PRINT Technology, Q-Sphera, SKS Microparticles, Verisome, Capsule Ring Device, MicroPump, Microneedle Injector, Microneedle/Needle-less Injectors, EyeCET, Gemini Refractive Capsule, and IVMED. Preferably, the eye implant technology is ApidCOR, BioSeizer-ProDex, Vitrasert, Retisert, Iluvien, I-Vation, Nanoporous Silicon, Ozurdex/Novadur, OcuLief, Port Delivery System (PDS), PEA Implant, PEG-PLA Microspheres, PRINT Technology, Q-Sphera, SKS Microparticles, Verisome, Capsule Ring Device, or MicroPump.

In some embodiments, the ocular disease is glaucoma. In some embodiments, therapeutic efficacy in treating glaucoma is determined by detecting a reduction in intraocular pressure, or a reduction in the rate of optic nerve damage/retinal nerve fiber layer thinning, amount sufficient to relieve or prevent optic nerve damage. In further embodiments, the therapeutic efficacy of the treatment is determined by improvement of optic nerve head blood flow. In other embodiments, therapeutic efficacy of treating glaucoma is determined by measuring an improvement in retinal, optic nerve head or tissue perfusion.

In some embodiments for the treatment of glaucoma, the regimen further comprises the addition of a therapeutically effective amount of an intra-ocular pressure (IOP) reducing agent or a neuroprotective agent, or a pharmaceutically acceptable salt of any of the foregoing. In some embodiments, the IOP reducing agent is selected from the group consisting of prostaglandins (such as latanoprost or travoprost), beta-blockers (such as timolol or betaxolol), alpha adrenergic agonists (such as brimonidine, apraclonidine), carbonic anhydrase inhibitors (such as dorzolamide or brinzolamide), Rho kinase inhibitors (such as netarsudil) and miotic or cholinergic agents (such as pilocarpine). In some embodiments, the neuroprotective agent is selected from the group consisting of anti-apoptotic agents (such as caspase-2 inhibitor) and neurotrophic factors (such as ciliary neurotrophic factor).

In some embodiments, the ocular disease is diabetic retinopathy (DR). In further embodiments, therapeutic efficacy of treating DR is determined by a decrease in retinal neovascularization, diabetic retinopathy severity score and neurodegeneration induced by diabetes. In other embodiments, therapeutic efficacy of treating DR is determined by measuring an improvement in retinal or choroid perfusion.

In some embodiments, the disease is retinal vein occlusion (RVO). In further embodiments, therapeutic efficacy of treating RVO is determined by measuring an improvement in tissue perfusion, a reduction in inflammation, or a combination of the foregoing.

In some embodiments, the disease is NAION. In further embodiments, therapeutic efficacy of treating NAION is determined by measuring an improvement in tissue perfusion, a reduction in inflammation, or a combination of the foregoing.

In some embodiments, the disease is AION. In further embodiments, therapeutic efficacy of treating AION is determined by measuring an improvement in tissue perfusion, a reduction in inflammation, or a combination of the foregoing.

In some embodiments, the ocular disease is retinopathy of prematurity (ROP). In further embodiments, therapeutic efficacy of treating ROP is determined by measuring an improvement in retinal perfusion and reduction in abnormal neovascularization.

In some embodiments, the endothelin receptor antagonist or a pharmaceutically acceptable salt thereof is Edonentan. In other embodiments, the endothelin receptor antagonist or a pharmaceutically acceptable salt thereof is A-182086. In either case, the antagonist or its pharmaceutically acceptable salt can be in a crystalline form or an amorphous form, each of which can be for pharmacologically acceptable use.

In some embodiments, the endothelin receptor antagonist is administered in a dosage between about 1 μg and about 4 mg (e.g., between about 1 μg and about 10 μg, between about 10 μg and about 100 μg, between about 100 μg and about 500 μg, and between about 500 μg and about 4 mg). In some embodiments, the endothelin receptor antagonist is administered in a dosage between about 0.1 μg and about 10 μg. In some embodiments, the endothelin receptor antagonist is administered in a dosage between about 1 μg and about 10 μg. In further embodiments, the endothelin receptor antagonist is administered in a dosage between about 10 μg and about 100 μg.

In further embodiments, the endothelin receptor antagonist is administered in a dosage between about 100 μg and about 500 μg, and between about 500 μg and about 4 mg.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof.

The details of one or more embodiments of the disclosure are set forth in the description below. Other features, objects, and advantages of the disclosure will be apparent from the below drawings, description and from the claims.

BRIEF DESCRIPTION OF THE DRAWINGS

FIG. 5A and FIG. 5B reveal prevented RGC loss and maintained RGC function after treatment with Edonentan.

FIG. 5C reveals the ability of Edonentan to permeate through cornea/sclera and achieve retina exposure after topical administration.

FIG. 6A and FIG. 6B reveal prevented RGC loss and maintained RGC function after treatment with A-182086.

FIG. 6C reveals the ability of A-182086 to permeate through cornea/sclera and achieve retina exposure after topical administration.

DETAILED DESCRIPTION

Figure 1:
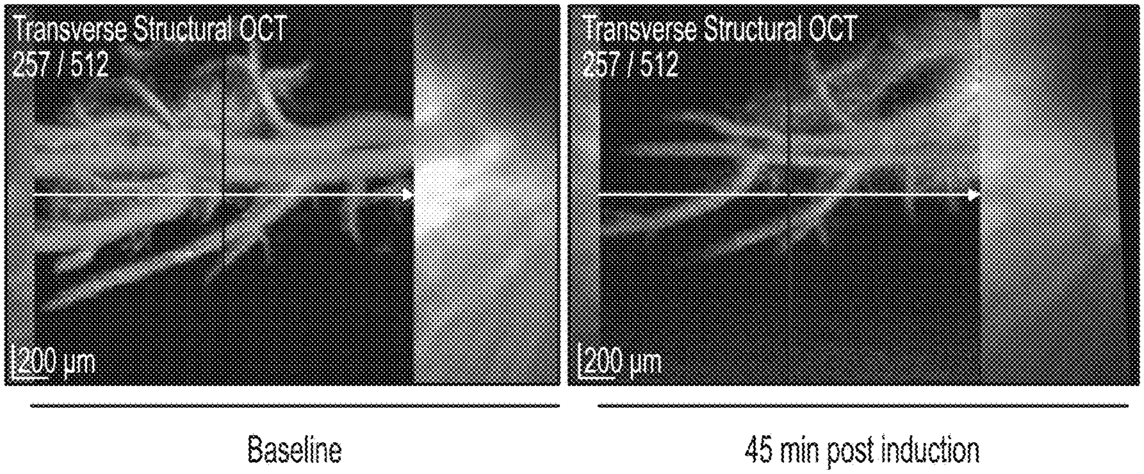
FIG. 1 depicts optical coherence tomography-angiography (OCT-A) images of a representative experiment revealing severe vasospasm in the rabbit retinal vascular structure in focus 45 min after 0.5 μg of Endothelin-1 (ET-1) administration via intravitreal injection (IVT) injection.

The present invention arises from the discovery that Edonentan and A-182086 can be used to prevent, treat or otherwise ameliorate ocular diseases including, but not limited to, glaucoma, diabetic retinopathy (DR), retinal vein occlusion (RVO), non-arteritic anterior ischemic optic neuropathy (NAION), arteritic anterior ischemic optic neuropathy (AION), and retinopathy of prematurity (ROP). The invention is further described below.

Endothelin Receptor Antagonists

Methods of the present invention include contacting the eye tissue (topically or intra-ocularly) with or administration of a therapeutically effective amount of Edonentan and A-182086, or a pharmaceutically acceptable salt thereof. The antagonists are specifically Edonentan and A-182086, as described below.

Methods of preparing Edonentan are well known to a person of skill in the art. Suitable methods are disclosed, for example, in U.S. Pat. No. 6,043,265. Edonentan has the chemical name of N-[[2'-[[(4,5-dimethyl-3-isoxazolyl)amino]sulfonyl]-4-(2-oxazolyl)[1,1'-biphenyl]-2-yl]methyl]-N,3,3-trimethylbutanamide (molecular weight of 536.6 g/mol) and the structure:

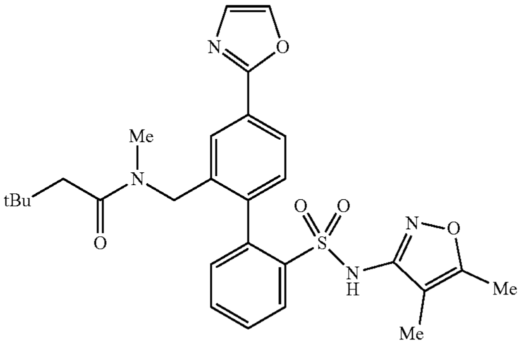

Edonentan

Methods of preparing A-182086 are well known to a person of skill in the art. Suitable methods are disclosed, for example, in U.S. Pat. No. 6,162,927. A-182086 has the chemical name of (2R,3R,4S)-4-(2H-1,3-benzodioxol-5-yl)-2-(3-fluoro-4-methoxyphenyl)-1-[2-(N-propylpentane-1-sulfonamido)ethyl]pyrrolidine-3-carboxylic acid (molecular weight of 578.7 g/mol) and the structure:

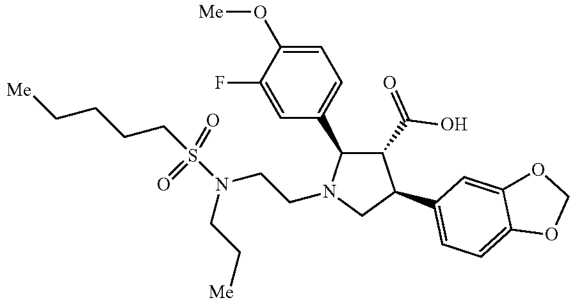

A-182086

Ocular Diseases

The methods of the present disclosure include the use of Edonentan and A-182086 described above in the treatment and amelioration of an ocular disease selected from glaucoma, diabetic retinopathy (DR), retinal vein occlusion (RVO), non-arteritic anterior ischemic optic neuropathy (NAION), arteritic anterior ischemic optic neuropathy (AION), and retinopathy of prematurity (ROP), which are described below.

Glaucoma

In the treatment of glaucoma using Edonentan or A-182086 described herein, a "therapeutically effective amount" can be determined by assessing an improvement in retinal blood flow (RBF) over what could be achieved by the standard of care (lowering of intra-ocular pressure (IOP)). For a glaucoma indication, the improvement in blood flow in the healthy rabbit ocular model can be used as predictive of pharmacodynamic response (PD) in humans. Rabbits are commonly used to assess ocular PK/PD relationship for compounds targeting human ocular diseases due to the anatomic and functional similarities of the rabbit and human eye. Previously, intravitreal administration of ET-1 into the rabbit eye has been shown to induce significant vasoconstriction and optic nerve damage (Sasaoka M. et al, Exp Eye Res 2006; Sugiyama T. et al, Arch Ophthalmol 2009). Efficacy in this model is benchmarked to the reversal of perfusion impairment induced by intravitreal ET-1 administration at certain concentrations. For example, the efficacy can be achieved at a concentration equivalent to the levels observed in human glaucoma patients' plasma and aqueous humor (Li S. et al, Journal of Ophthalmology 2016).

Other examples of relevant animal glaucoma models are Morrison's rat model of elevated IOP and the laser-induced non-human primate (NHP) glaucoma model. Glaucoma in Morrison's rat model is induced by sustained elevation of IOP through hypertonic saline administration via episcleral veins. In the laser-induced NHP glaucoma model, after sustained elevation of IOP, optic nerve head blood flow has been shown to be reduced (Wang L. et al, Invest Ophthalmol Vis Sci 2012). Furthermore, the reduction in optic nerve head blood flow has been shown to correlate with long-term structural changes in the optic nerve (Cull G. et al, Invest Ophthalmol Vis Sci 2013).

Efficacy in the above-described glaucoma models is defined as reduction in IOP, improvement in optic nerve head or retinal blood flow from baseline, prevention or slowing of the progression of structural neurodegenerative changes such as retinal nerve fiber layer thickness as measured by optical coherence tomography (OCT) or retinal ganglion cell counts on flat mount as well as functional changes such as electroretinography (ERG) or contrast sensitivity after treatment with Edonentan or A-182086.

It is believed that the effect of Edonentan or A-182086 on retinal blood flow can be assessed by the blood vessel radius (r) in Poiseuille's Law. An increase in (r) with an endothelin antagonist, would induce a more pronounced increase in blood flow than what can be achieved by an increase in perfusion pressure through IOP reduction:

$$\text{Blood flow}=(\text{perfusion pressure}\times\pi r^4)/(8\eta l)$$

where l: blood vessel length r: blood vessel radius $\eta$: blood viscosity perfusion pressure: mean arterial pressure—IOP Furthermore, Edonentan or A-182086 may reduce IOP and/or prevent RGC death through mechanisms independent of improvement in retinal/optic nerve head tissue perfusion. Accordingly, by using certain specific endothelin receptor antagonists, one (r) or more (IOP) of the above parameters can be altered to improve the RBF, thereby achieving therapeutic efficacy in treating glaucoma.

In some embodiments, the glaucoma patients are started on treatment as soon as they are diagnosed. In some embodiments, Edonentan or A-182086 is administered locally to the back of the eye using an intravitreal, topical, suprachoroidal, or implant delivery platform with a frequency of every 3 to 12 (e.g., every 3 to 6 or every 4 to 6) months.

Diabetic Retinopathy (DR)

Diabetes can cause serious late complications which are classified as microangiopathic (retinopathy, neuropathy and diabetic nephropathy) and macroangiopathic (cardiovascular disease). Diabetic retinopathy is the result of damage to the small blood vessels and neurons of the retina. The earliest changes leading to diabetic retinopathy include narrowing of the retinal arteries associated with reduced retinal blood flow; dysfunction of the neurons of the inner retina, followed in later stages by changes in the function of the outer retina, associated with subtle changes in visual function; dysfunction of the blood-retinal barrier, which protects the retina from many substances in the blood (including toxins and immune cells), leading to the leakage of blood constituents into the retinal neuropile. Later, the basement membrane of the retinal blood vessels thickens, capillaries degenerate and lose cells, particularly pericytes and vascular smooth muscle cells. This leads to loss of blood flow and progressive ischemia, and microscopic aneurysms which appear as balloon-like structures jutting out from the capillary walls, which recruit inflammatory cells; and lead to advanced dysfunction and degeneration of the neurons and glial cells of the retina.

Ischemia and oxidant injury observed in DR compromises blood flow and tissue ischemia which we have discovered can be reversed by Edonentan and A-182086. For DR indication, the improvement in retinal perfusion is anticipated to reduce hypoxia and suppress vascular endothelial growth factor (VEGF) upregulation with a resultant benefit of slowing vascular proliferative changes, neovascularization and/or macular edema complications.

As a surrogate model for the ischemic retinopathy changes observed in DR, a preclinical mouse model of retinopathy of prematurity (ROP) can be used. Oxygen-induced retinopathy in the mouse is a reproducible and quantifiable proliferative retinal neovascularization model suitable for examining pathogenesis and therapeutic intervention for retinal neovascularization in ROP and other vasculopathologies including DR. The model is induced by exposure of one-week-old C57BL/6J mice to 75% oxygen for 5 days and then to room air as previously described (Smith L E H et al., Invest Ophthalmol Vis Sci 1994). Efficacy in this preclinical model of ROP can be assessed by studying retinal hypoxia and neovascularization. The current standard of care in DR includes anti-VEGF therapies which only address advanced vascular complications of disease. In some embodiments, the patients with DR are started on this treatment during the non-proliferative stages of the disease. In some embodiments, either Edonentan or A-182086 is administered locally to the back of the eye using an intravitreal, topical, suprachoroidal, or implant delivery platform with a frequency of every 3 to 12 (e.g., every 3 to 6 or every 4 to 6) months.

Retinal Vein Occlusion (RVO)

Retinal vein occlusion (RVO), a vascular disorder of the retina, is currently treated with intravitreal injection of anti-VEGF drugs to inhibit the growth factor that causes macular edema and corticosteroids to combat the inflammatory components which lead to edema. It is highly desirable to use Edonentan and A-182086 therapies for treating RVO by improving tissue perfusion and reducing inflammation while avoiding the unwanted effects of systemic immunosuppression and/or local adverse effects of steroids.

RVO is currently treated with intravitreal steroids and anti-VEGF agents. We that improving perfusion of existing vessels will reduce the degree of macular edema and VEGF upregulation and the downstream maladaptive changes that manifests as RVO. To test efficacy, a preclinical mouse model of ischemic retinopathy can be used. Oxygen-induced retinopathy in the mouse is a reproducible and quantifiable proliferative retinal neovascularization model suitable for examining pathogenesis and therapeutic intervention for retinal neovascularization in many ischemic retinopathies including RVO. The model is induced by exposure of one-week-old C57BL/6J mice to 75% oxygen for 5 days and then to room air as previously described (Smith L E H et al., Invest Ophthalmol Vis Sci 1994). The efficacy in this preclinical model of ischemic retinopathy can be assessed by studying retinal hypoxia and neovascularization. A "therapeutically effective amount" of Edonentan or A-182086 described herein can be additive to the current standard of care by improving tissue perfusion and reducing inflammation mediated by ET-1 while avoiding the unwanted effects of local steroids. In some embodiments of treating RVO, the Edonentan or A-182086 is administered locally to the back of the eye using an intravitreal, topical, suprachoroidal, or implant delivery platform. The frequency of administration will vary based on a patient's disease course and response to therapy.

Non-Arteritic Anterior Ischemic Optic Neuropathy (NAION)

In Non-Arteritic Anterior Ischemic Optic Neuropathy (NAION), there is an interruption of blood flow to the small vessels which supply the anterior portion of the optic nerve. Vision loss in NAION is painless, rapid, and usually permanent. Risk factors for NAION include atherosclerosis (as this impairs blood flow through the blood vessels which supply the optic nerve) and a "tight" optic nerve. Also called "a disc at risk", an optic nerve with a small or absent optic cup makes a "tight" passage through the sclera as it enters the eye. This tight passage through the sclera is believed to place further pressure on the small vessels that supply the optic nerve. As atherosclerosis causes an increase in the outer diameter (and a decrease in the inside diameter) of these small vessels, there is no room for the vessels to expand as they are confined by the "tight" optic nerve. This process eventually leads to a loss of adequate blood flow to the optic nerve and Ischemic Optic Neuropathy ensues. Attempts to treat NAION have included radial neurotomy in order to relieve the mechanical pressure on the optic nerve and its supporting vasculature. This procedure carries all of the risks of intraocular surgery and is difficult to perform. The area being perforated is exquisitely delicate as are the surrounding structures. Collateral damage to these structures is not uncommon.

For NAION, there are no relevant preclinical models to test efficacy with endothelin antagonism. In addition, there are no approved therapies for non-arteritic anterior ischemic optic neuropathy. For treatment of NAION, a "therapeutically effective" amount of an endothelin antagonist would be one which causes a clinically meaningful improvement in visual acuity and/or visual field by increasing the perfusion of the optic nerve. As a predictor of this clinical endpoint, improvement in optic nerve head perfusion assessed by laser flowmeter or optical coherence tomography-A (OCT-A) and anatomical changes in retinal nerve fiber layer (RNFL) thickness determined by (OCT) will be used. In some embodiments, the medication is administered locally to the back of the eye using an intravitreal, topical, suprachoroidal, or implant delivery platform with a frequency of every 4 to 6 weeks as needed based on patient's disease course and response to therapy. For example, the medication is administered locally to the back of the eye using an intravitreal injection of a suspension with a frequency of every 5 weeks as needed based on patient's disease course and response to therapy.

Arteritic Anterior Ischemic Optic Neuropathy (AION)

Arteritic Anterior Ischemic Optic Neuropathy (AION) is an acute, often painful optic neuropathy that occurs predominantly in elderly patients over age 50 but with increasing incidence each decade thereafter and can cause permanent loss of vision. Ischemia occurs at the head of the optic nerve in relation with structural crowding of the nerve fibers, impairing perfusion and leading to optic disc edema. There is thought to be a genetic component to the disease, as evidence shows Caucasians are affected at a higher rate, but it has been reported in many different races and ethnicities.

Manifestations include rapid onset of unilateral visual loss accompanied by decreased visual acuity (typically severe: <20/200 in over 60% of the patients), visual field defects (altitudinal field defect is most common) or both. For AION, there are no relevant preclinical models to test efficacy with endothelin antagonism. In addition, there are no approved therapies for non-arteritic anterior ischemic optic neuropathy; however steroids have been traditionally used in most patients. Without treatment, visual loss occurs in 54-95% of GCA patients (16), typically within four months (10). With corticosteroid therapy, the rate of such decline is reduced to an estimated 13% (16). Visual recovery of the affected eye that has treatment is poor with a 15-34% improvement rate, which is higher with intravenous therapy. Worsening visual acuity has been reported in 9-17% despite therapy. Vision loss in both eyes is possible; however, most cases have indicated it to be frequently when one patient is unaware of vision loss in the first eye. The incidence of having this bilateral involvement involves timing heavily as well as how aggressively corticosteroid therapy is utilized. However, if left untreated, bilateral vision loss can proceed quickly from either optic nerve, retinal or choroidal ischemia in up to 50% of cases. For treatment of AION, a "therapeutically effective" amount of an endothelin antagonist would be one which causes an additive improvement in visual acuity achieved by steroids by improving perfusion of the optic nerve and the retina. As a predictor of improvement in visual acuity and/or visual field, improvement in optic nerve head perfusion assessed by laser flowmeter or OCT-A and anatomical changes in retinal nerve fiber layer (RNFL) thickness determined by optical coherence tomography (OCT) will be used. In some embodiments, the medication is administered locally to the back of the eye using an intravitreal, topical, suprachoroidal, or implant delivery platform with a frequency of every 4 to 6 weeks as needed based on patient's disease course and response to therapy. For example, the medication is administered locally to the back of the eye using an intravitreal injection of a suspension with a frequency of every 5 weeks as needed based on patient's disease course and response to therapy.

Retinopathy of Prematurity (ROP)

Retinopathy of prematurity (ROP) is a retinal vasoproliferative disease that affects premature infants. ROP continues to be a major preventable cause of blindness and visual handicaps globally. With improved perinatal care, improved survival of moderately preterm infants, and limited resources for oxygen delivery and monitoring, more mature preterm infants are developing severe ROP in developing countries.

The pathophysiology of ROP is characterized by two phases. Phase I ROP is due to vaso-obliteration beginning immediately after birth secondary to a marked decrease in VEGF and insulin-like growth factor-1 (IGF-1). Phase II begins around 33 weeks' postmenstrual age (PMA). During this phase, VEGF levels increase, especially if there is retinal hypoxia with increasing retinal metabolism and demand for oxygen leading to abnormal vasoproliferation. For advanced stages of ROP, laser ablation of avascular retina, early treatment of ROP (ETROP) protocol, intravitreal injection of anti-VEGF antibodies (e.g. bevacizumab) and vitrectomy are used to protect central vision and prevent retinal detachment. Long-term complications such as refractory errors, recurrence of ROP and risk of retinal detachment require continued follow-up with an ophthalmologist through adolescence and beyond.

ROP is induced by severe ischemia due to underdevelopment of retinal vessels secondary to premature birth. Therefore, as an aspect of the invention, we believe that improving perfusion of existing vessels with Edonentan or A-182086 will reduce the degree of ischemia and VEGF upregulation and the downstream maladaptive changes that manifests as ROP. To test efficacy, a preclinical mouse model of ROP can be used. Oxygen-induced retinopathy in the mouse is a reproducible and quantifiable proliferative retinal neovascularization model suitable for examining pathogenesis and therapeutic intervention for retinal neovascularization in ROP. The model is induced by exposure of one-week-old C57BL/6J mice to 75% oxygen for 5 days and then to room air as previously described (Smith L E H et al., Invest Ophthalmol Vis Sci 1994). The efficacy in this preclinical model of ROP can be assessed by studying retinal hypoxia and neovascularization. A "therapeutically effective amount" of Edonentan or A-182086, as described herein will be additive to the current standard of care by improving tissue perfusion and reducing pathologic neovascularization induced by VEGF. In some embodiments, the medication is administered locally to the back of the eye using an intravitreal, topical, suprachoroidal, or implant delivery platform with a frequency of every 4 to 6 weeks as needed based on patient's disease course and response to therapy. For example, the medication is administered locally to the back of the eye using an intravitreal injection with a frequency of every 5 weeks as needed based on patient's disease course and response to therapy.

Pharmaceutical Compositions

Some embodiments described herein relates to a pharmaceutical composition, that can include a therapeutically effective amount of one of Edonentan and A-182086, described herein, or a pharmaceutically acceptable salt thereof, and a pharmaceutically acceptable carrier, diluent, excipient or combination thereof. Such antagonist or its pharmaceutically acceptable salt can be in a crystalline form or an amorphous form, each of which can be for pharmacologically acceptable use.

The term "pharmaceutical composition" refers to a mixture of one or both compounds disclosed herein with other chemical components, such as diluents or carriers. The pharmaceutical composition facilitates administration of the compound to an organism. Pharmaceutical compositions will generally be tailored to the specific intended route of administration.

Some pharmaceutical compositions involve preparing a pharmaceutically acceptable salt. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the invention can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts, see Berge et al., 66 J. PHARM. SCI., 1-19 (1977).

The term "pharmaceutically acceptable" defines a carrier, diluent, excipient, salt or composition that is safe and effective for its intended use and possesses the desired biological and pharmacological activity.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, levigating, emulsifying, encapsulating or entrapping processes. See, e.g., Encapsulation Processes, in: Food Powders, 2005, 199-299. Additionally, the active ingredients are contained in an amount effective to achieve its intended purpose. Compounds used in the pharmaceutical combinations disclosed herein may be provided as pharmaceutically acceptable salts.

It is preferred to administer the compounds or pharmaceutical compositions of this invention in a local manner either as a topical ophthalmic formulation or via injection of the compounds or pharmaceutical compositions directly to the ocular tissue, often in a depot or sustained release formulation. The manner of local administration can be intravitreal, suprachoroidal, periocular, or subconjunctival injection of a formulation, or use of an implant technology or topical application. For example, the compound is administered in a liposomal preparation that slowly releases the compound sustaining the desired pharmacological effects. Alternatively, polyvinyl alcohol nanoparticles can be prepared by well-known methods to afford a sustained or extended release-formulation for topical or intra-ocular application.

Furthermore, one may administer the compound in a targeted drug delivery system. Examples of a targeted drug delivery system include, but are not limited to, ApidCOR, BioSeizer-ProDex, Vitrasert, Retisert, Iluvien, I-Vation, Nanoporous Silicon, Ozurdex/Novadur, OcuLief, Port Delivery System (PDS), PEA Implant, PEG-PLA Microspheres, PRINT Technology, Q-Sphera, SKS Microparticles, Verisome, Capsule Ring Device, MicroPump, Microneedle Injector, Microneedle/Needle-less Injectors, EyeCET, Gemini Refractive Capsule, IVMED, Ciliary Sulcus Ring, Episcleral Exoplant, Eye-D Implant, and Nanoliposomes.

In some embodiments, the targeted drug delivery system that can be used in the methods of this disclosure is selected from ApidCOR, BioSeizer-ProDex, Vitrasert, Retisert, Iluvien, I-Vation, Nanoporous Silicon, Ozurdex/Novadur, OcuLief, Port Delivery System (PDS), PEA Implant, PEG-PLA Microspheres, PRINT Technology, Q-Sphera, SKS Microparticles, Verisome, Capsule Ring Device, MicroPump, Microneedle Injector, Microneedle/Needle-less Injectors, EyeCET, Gemini Refractive Capsule, and IVMED. Preferably, the targeted drug delivery system is ApidCOR, BioSeizer-ProDex, Vitrasert, Retisert, Iluvien, I-Vation, Nanoporous Silicon, Ozurdex/Novadur, OcuLief, Port Delivery System (PDS), PEA Implant, PEG-PLA Microspheres, PRINT Technology, Q-Sphera, SKS Microparticles, Verisome, Capsule Ring Device, or MicroPump.

In some embodiments, the pharmaceutical composition is an ophthalmic preparation comprising a therapeutically effective amount of one or more endothelin receptor antagonists described herein, or a pharmaceutically acceptable salt thereof. As used herein, an "ophthalmic preparation" refers to a specialized dosage form designed to be instilled onto the external surface of the eye (topical), administered inside (intraocular) or adjacent (periocular) to the eye or used in conjunction with an ophthalmic device. In some embodiments, the ophthalmic preparation is in the form of a solution, suspension, or an ointment. In other embodiments, the ophthalmic preparation is in the form of a gel, a gel-forming solution, an ocular insert, a micro/nanoparticle preparations for topical or preferably intravitreal injection, or an implant.

In some embodiments, the ophthalmic preparation comprises a preservative. Examples of suitable preservatives include, but are not limited to, cationic wetting agents (e.g. benzalkonium chloride), organic mercurials (e.g., phenylmercuric nitrate, phenylmercuric acetate), organic acids or their esters (e.g., sorbic acid, esters of p-hydroxybenzoic acid such as methyl hydroxybenzoate, propylhydroxybenzoate), and alcohol substitutes (e.g., chlorobutanol, phenylethanol). The preservative can be present in the ophthalmic preparation in an amount in the range of about 0.002% w/v to about 0.5% w/v (e.g., 0.01-0.25% w/v). The ophthalmic preparation can further comprise a preservative aid. Examples of suitable preservative aid include, but are not limited to, ethylenediaminetetraacetic acid (EDTA).

In some embodiments, the ophthalmic preparation comprises one or more additional excipients or agents to impart viscosity or lubrication, stabilize the active ingredients against decomposition, increase solubility of an active or inactive ingredient, adjust tonicity, or act as solvent. Examples of excipients or agents for imparting viscosity or lubrication include hypromellose, carbomer 974P, hydroxyethyl cellulose (HEC), polyvinyl alcohol, sodium hyaluronate, sodium carboxymethyl cellulose, Carbopol 940, hydroxypropylmethyl cellulose (HPMC), poloxamer, xyloglucan, alginic acid, sodium alginate, gellan gum, cellulose acetate phthalate, and xantham gum. Examples of excipients or agents as stabilizers include sodium bisulfite, sodium metabisulfite, sodium thiosulfate, and sodium sulfate/sulfuric acid, which can act as antioxidants. Examples of excipients or agents as solubilizers include, but are not limited to, providone, creatinine, castor oil, and cyclodextrin (e.g., γ-cyclodextrin). Examples of excipients or agents for adjusting tonicity include, but are not limited to, sodium chloride, potassium chloride, calcium chloride dehydrate, magnesium chloride hexahydrate, sugars (e.g., sucrose, maltose, dextrose, etc.), glycerin, propylene glycol, mannitol, ascorbic acid, and acetylcysteine.

In some embodiments, the ophthalmic preparation comprises one or more buffers to adjust pH. Examples of buffers for adjusting pH include, but are not limited to, sodium citrate, monobasic sodium phosphate, dibasic sodium phosphate, boric acid, hepatahydrate, sodium acetate trihydrate, sodium citrate dihydrate, histidine, and phosphate buffered saline (PBS). The resulting composition can have a pH value of 5.0-8.5 (e.g., 5.0-6.0, 5.2-5.8, 6.0-8.0, 6.6-7.8, 6.2-8.2, and 6.2-7.5)

In some embodiments, the ophthalmic preparation comprises one or more surfactants. Examples of surfactants include sorbitan ether esters of oleic acid (e.g., polysorbate or Tween 20 and 80) and tyloxapol.

The volume that can be injected to a human eye at one time is around 50-90 μL through the intravitreal route, up to 450 μL through a subretinal route, up to 200 μL via suprachoroidal routes, and about 40-50 μL via topical route (e.g. topical administration as an eye drop). The needle used in these routes is typically 27 to 30 G in size. The dose depends on the concentration that can be formulated to fit this volume, potency, target efficacy and pharmacokinetic profile for each indication. Generally, the injections to the eye will not be administered at a frequency greater than once per month per eye. For topical administrations (e.g. eye drop), in most instances, the frequency of administration to the eye does not exceed more than once or twice a day.

In some embodiments, the intravitreal formulation will comprise a dose of the endothelin receptor antagonist in the range of about 1 μg to about 1 mg. A first exemplary formulation comprises about 1 μg to about 1 mg of an endothelin receptor antagonist described above, about 10 mM histidine HCl, about 10% α,α-trehalose dihydrate, and about 0.01% polysorbate 20. A second exemplary formulation comprises about 1 μg to about 1 mg of endothelin receptor antagonist, about 10 mM sodium phosphate, about 40 mM sodium chloride, about 0.03% polysorbate 20, and about 5% sucrose.

In some embodiments, the intravitreal formulation will comprise a dose of the endothelin receptor antagonist in the range of about 10 μg to about 100 μg. A first exemplary formulation comprises about 10 μg to about 100 μg of an endothelin receptor antagonist described above, about 10 mM histidine HCl, about 10% α,α-trehalose dihydrate, and about 0.01% polysorbate 20. A second exemplary formulation comprises about 10 μg to about 100 μg of endothelin receptor antagonist, about 10 mM sodium phosphate, about 40 mM sodium chloride, about 0.03% polysorbate 20, and about 5% sucrose.

In further embodiments, the intravitreal formulation will comprise a dose of the endothelin receptor antagonist in the range of about 500 μg to about 4 mg. A first exemplary formulation comprises about 500 μg to about 1 mg of an endothelin receptor antagonist described above, about 0.014% potassium phosphate monobasic, 0.08% sodium phosphate dibasic, 0.7% sodium chloride, 0.02% polysorbate, and 0.5% sodium carboxymethyl cellulose. A second exemplary formulation comprises about 500 μg to about 1 mg of an endothelin receptor antagonist described above, about 0.04% sodium phosphate monobasic monohydrate, about 0.3% sodium phosphate dibasic heptahydrate, 0.63% sodium chloride, and about 1% to about 2.3% sodium hyaluronate.

Without further elaboration, it is believed that one skilled in the art can, based on the above description, utilize the present invention to its fullest extent. The following specific examples, i.e., Examples 1-8, are therefore to be construed as merely illustrative, and not limitative of the remainder of the disclosure in any way whatsoever.

EXAMPLES

Example 1: Compound Physicochemical and Biochemical Characterization

Provided in Table 1 below are physicochemical and biochemical data for Edonentan and A-182086 described above. As indicated in Table 1, at pH 2, A-182086 has a solubility superior to that of Edonentan. On the other hand, at pH 7, Edonentan has a solubility superior to that of A-182086.

TABLE 1

Compound physicochemical and biochemical characterization

| Compound | Edonentan (MW = 537) | A-182086 (MW = 578) |
|---|---|---|
| Functional Potency for $ET_A$ and $ET_B$ Receptors | $ET_A$ $IC_{50}$ = 1.54 nM<br>$ET_B$ $IC_{50}$ = 590 nM<br>High potency<br>High specificity | $ET_A$ $IC_{50}$ = 0.63 nM<br>$ET_B$ $IC_{50}$ = 3.48 nM<br>High potency<br>Low specificity |
| Solubility at pH 2 | <0.54 μg/mL;<br><1 μM | 92.5 μg/mL<br>159.8 μM |
| Solubility at pH 7[a] | 326 μg/mL;<br>607 μM | 172.7 μg/mL;<br>298.4 μM |
| Solubility in Ethyl Acetate | >8900 mg/mL;<br>>16753 mM<br>Good | >10620 mg/mL;<br>>18351 mM<br>Good |
| Stability in Solid State (2 h @ 125° C.) | Stable | about 87% remaining/ unstable |
| LogD @ pH 7.4 | 1.48 | 2.30 |
| Permeability (PAMPA—log $P_e$) (PSA[b]) | log $P_e$ = −5.9<br>PSA = 109.66<br>Mid-High Permeability | log $P_e$ = −5.1<br>PSA = 105.61<br>Mid-High Permeability |

[a]The data are from the amorphous form.

[b]Calculated property that considers surface charge distributions (mainly O and N). Compounds with a PSA around 90 or below would be predicted to cross the blood-brain barrier.

In the above table, the physicochemical data, e.g., solubility, were obtained following standard protocols known in the field (see, e.g., Reis et al., Mini Rev Med Chem., 2010, 10(11): 1071-6; Avdeef et al., Expert Opin Drug Metab Toxicol., 2005, 1(2):325-42; Bharate et al., Comb Chem High Throughput Screen., 2016, 19(6):461-9; and Jain et al., J Pharm Biomed Anal., 2013, 86:11-35.); and the biochemical data, i.e., potency for $ET_A$/$ET_B$, were obtained following the protocols known in the field (see, e.g., Kirkby et al., Br J Pharmacol., 2008, 153(6): 1105-19; and Maguire et al., Br J Pharmacol., 2014, 171(24):5555-72.).

Example 2: Formulation of Edonentan for Intravitreal Use in Rabbit

An appropriate amount of Edonentan is dissolved in neat PEG400, followed by addition of a 15% CD (HP-β-cyclodextrin) solution. The final concentration of PEG400 is measured to be 20%. Target concentrations are 5 mg/ml and 0.5 mg/ml based on the amount of Edonentan. The resulting solution is filtered using a 0.25 micron filter.

Example 3: Effects of Edonentan and ET-1 in a Rabbit Model

Figure 2:
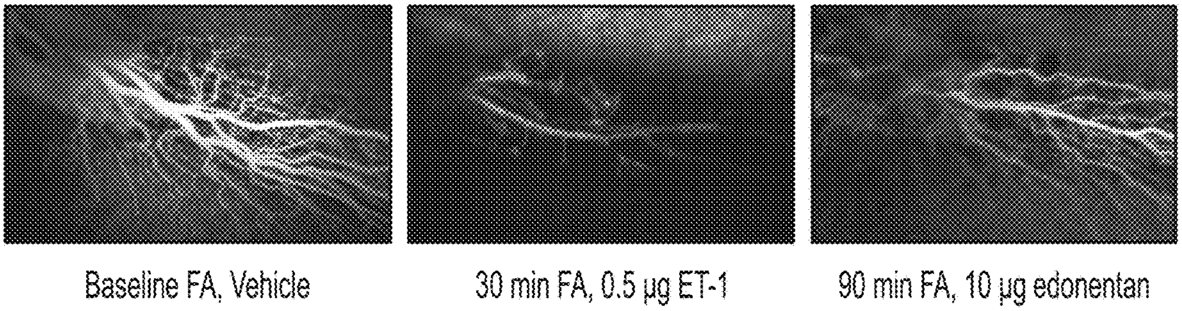
FIG. 2 depicts fluorescein angiography (FA) images revealing reversal of ET-1 induced vasospasm after IVT administration of 10 μg Edonentan.
Figure 3:
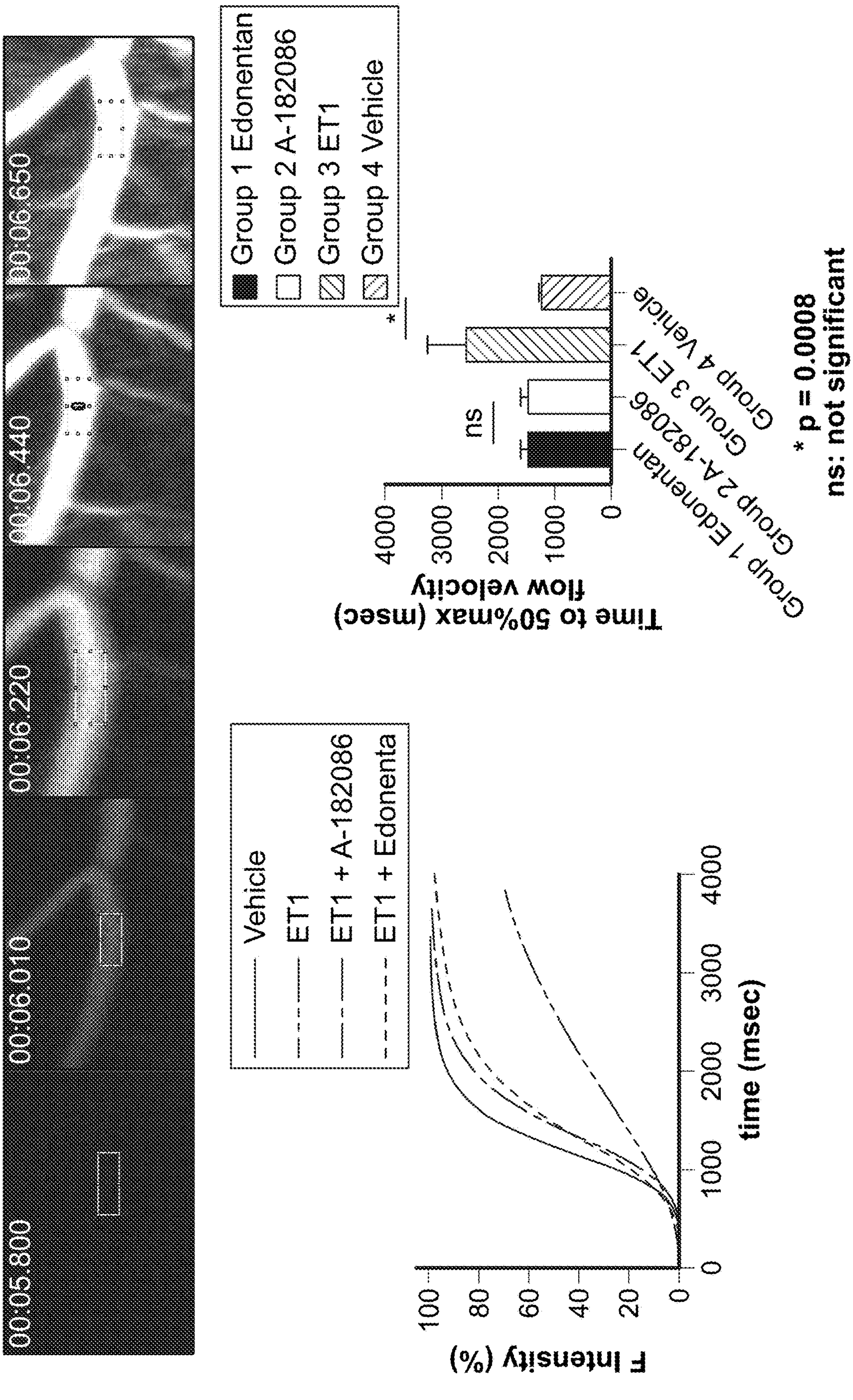
FIG. 3 depicts the comparison of fluorescein dye velocity as an index of retinal blood flow in healthy rabbits (n=5/group) after IVT administration of vehicle alone (control group), or 0.5 μg of ET-1 alone, or 0.5 μg of ET-1 and 10 μg of Edonentan, or 0.5 μg of ET-1 and 10 μg of A-182086—revealing prolongation of dye velocity/reduction of flow in ET-1 treated rabbits which is improved to control levels following treatment with Edonentan or A-182086.

Adult, male Dutch-belted rabbits were given a 20 μl intravitreal injection (IVT) of 0.5 μg of ET-1 followed by a 20 µl intravitreal injection of 10-100 µg Edonentan given 30 min after the ET-1 administration. IOP, optical coherence tomography-angiography (OCT-A), and fluorescein angiograms (FA) were performed at pre-specified time points (30, 45, 60, and 75 min) following ET-1 and Edonentan administration to assess retinal blood flow changes induced by ET-1+/−Edonentan. As shown in FIG. 1, ET-1 administration effectively induced a clear vasoconstriction in the retinal vascular beds within 45 min. FIG. 2 shows that the effect of ET-1 was then reversed with 10 µg of Edonentan administration within 90 min (60 min after Edonentan administration).

Example 4: Preparation of an Extended Release Formulation Containing Edonentan

A concentrated Edonentan dispersion is made by combining Edonentan with water, Vitamin E-TPGS and γ-cyclodextrin. These ingredients are mixed to disperse the Edonentan, and then autoclaved. Sodium hyaluronate may be purchased as a sterile powder or sterilized by filtering a dilute solution followed by lyophylization to yield a sterile powder. The sterile sodium hyaluronate is dissolved in water to make an aqueous concentrate. The concentrated Edonentan dispersion is mixed and added as a slurry to the sodium hyaluronate concentrate. Water is added in sufficient quaintly (q.s., as much as suffices, in this case as much as is required to prepare the homogenous mixture, dispersion, gel or suspension) and the mixture is mixed until homogenous. Examples of these compositions are provided in Table 2 below:

TABLE 2

Compositions of extended release formulation containing Edonentan

| | Composition A | Composition B |
|---|---|---|
| Edonentan | 2.0% (w/v) | 8.0% (w/v) |
| Sodium hyaluronate (polymeric) | 2.5% (w/v) | 2.3% (w/v) |
| Sodium chloride | 0.63% (w/v) | 0.63% (w/v) |
| dibasic sodium phosphate, heptahydrate | 0.30% (w/v) | 0.30% (w/v) |
| Monobasic sodium phosphate, monohydrate | 0.04% (w/v) | 0.04% (w/v) |
| Water for injection | q.s. | q.s. |

These exemplary compositions contain a sufficient concentration of high molecular weight (i.e. polymeric) sodium hyaluronate so as to form a gelatinous plug or drug depot upon intravitreal injection into a human eye. Preferably the average molecular weight of the hyaluronate used is less than 2 million, and more preferably the average molecular weight of the hyaluronate used is between about 1.3 million and 1.6 million. The Edonentan particles are, in effect, trapped or held within this viscous plug of hyaluronate, so that undesirable pluming does not occur upon intravitreal injection of the formulation. Thus, the risk of drug particles disadvantageously settling directly on the retinal tissue is substantially reduced, for example, relative to using a composition with a water-like viscosity, such as Kenalog® 40. Since sodium hyaluronate solutions are subject to dramatic shear thinning, these formulations are easily injected via 25 gauge, 27 gauge or even 30 gauge needles.

Example 5: Preparation of a Topical Edonentan Formulation

A topical Edonentan formulation can be prepared following a known method (e.g., WO 2016156639 A1). More specifically, 20 g of Cremophor® RH40 is dissolved in 75 mL of deionized water by magnetic stirring, which is allowed to stir until completely dissolved. Then 1.5 g of trometamol is added to the resulting solution and stirred for 15 minutes, achieving complete dissolution. 0.5 g of Edonentan is added and allowed to stir for 15 minutes, ensuring complete dissolution. Then 2 g of glycine and 1 g of boric acid are added and allowed to stir until completely dissolved. The resulting solution is added 100 mL deionized water in sufficient quantity. The final solution is filtered with filter paper, and a clear, colorless solution with a pH of 8.06 is obtained. The solution in dropper bottles eyedrop with a volume of 5 mL is packed.

Example 6: Topical Ophthalmic Solution Nanoparticles Containing Edonentan

Nanoparticles were prepared by solvent evaporation technique. A solution of 120 mg of 50:50 PLGA in 60 mL of ethyl acetate was prepared. To this solution it was incorporated under turboagitation an aqueous solution of 50 ml of water with 12 mg of Edonentan and 0.5 mg of polyvinyl alcohol. The resulting mixture was left under continuous agitation and under vacuum for 2 hours. Then the resulting preparation was ultra-centrifuged and washed with water three times to remove the nanoparticles from the medium. The nanoparticles thus obtained were dried in a vacuum oven and after evaluation, dispersed in an isotonic aqueous solution enough for a concentration of 5 mg/l mL of Edonentan.

Example 7: Glaucoma Preclinical Studies

The healthy rabbit model is used to assess the pharmacodynamic effect (in vivo) of Edonentan and or A-182086 or pharmaceutically acceptable salts thereof. These studies are conducted with varying doses of the selected endothelin antagonists. Additional animal studies are conducted by combining endothelin antagonists with the current standard of care. The Morrison's rat model of glaucoma, rat model of acutely elevated IOP and laser induced glaucoma model in the non-human primate are used to assess optic nerve head blood flow and rate of retinal ganglion cell loss with varying doses of the selected endothelin antagonists with and without standard of care.

The improvement in blood flow in the healthy rabbit model is measured for the indicated endothelin receptor antagonists at varying doses after induction of perfusion impairment by locally administered ET-1. The changes in optic nerve head blood flow and retinal nerve fiber layer (RNFL) thickness in the non-human primate glaucoma models are measured for the indicated endothelin receptor antagonists at varying doses. The results show an improvement of RGC survival, retinal and optic nerve head blood flow and slowing of RNFL thinning due to the use of selected endothelin receptor antagonists. Dosing regimens for humans are predicted from the results of the healthy rabbit and non-human primate glaucoma models.

Pharmacodynamic Study to Evaluate Changes Retinal Blood Flow in the Rabbit

Figure 8A:
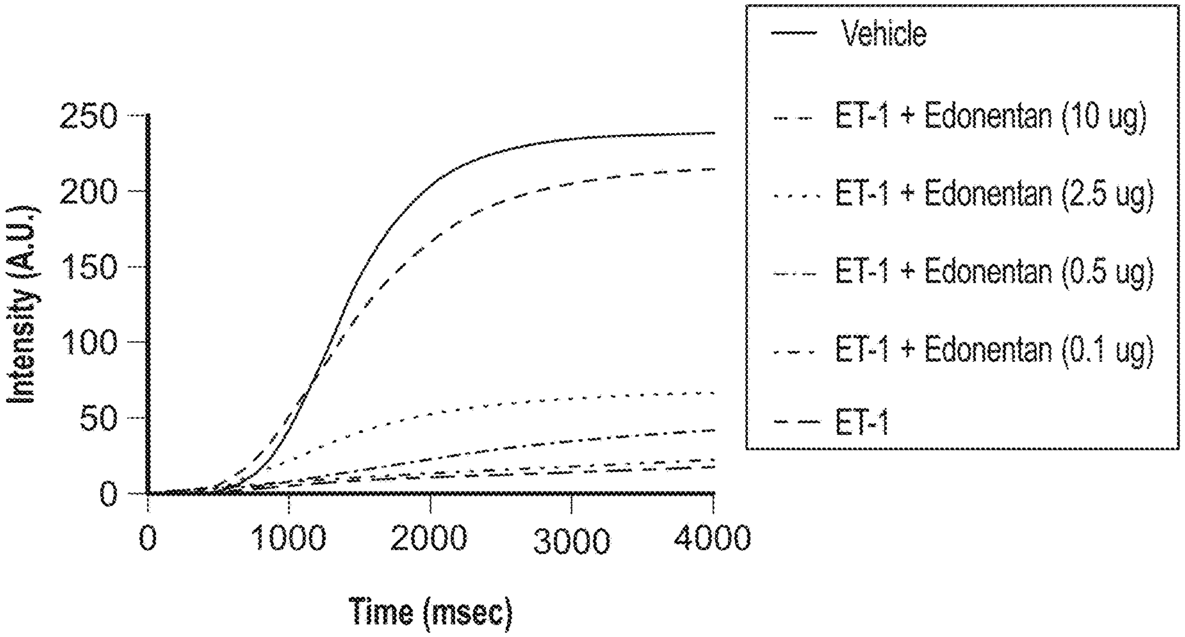
FIG. 8A and FIG. 8B depict the comparison of fluorescein dye velocity as an index of retinal blood flow in ET-1 induced rabbits (n=5 rabbits/group) after IVT administration of vehicle alone (control), 0.1 μg of ET-1 and 10 μg of Edonentan, 0.1 μg of ET-1 and 2.5 μg of Edonentan, 0.1 μg of ET-1 and 0.5 μg of Edonentan, 0.1 μg of ET-1 and 0.1 μg of Edonentan, or 0.1 μg of ET-1 alone—revealing dose-response in the rabbit ET-1 induced vasospasm model.
Figure 8B:
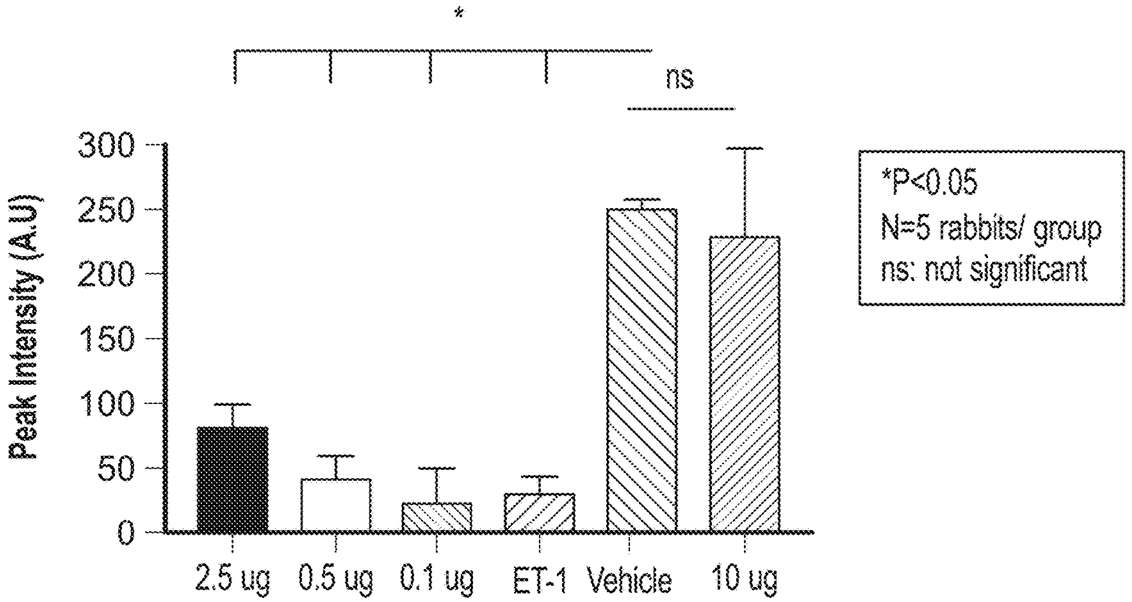
Figure 9A:
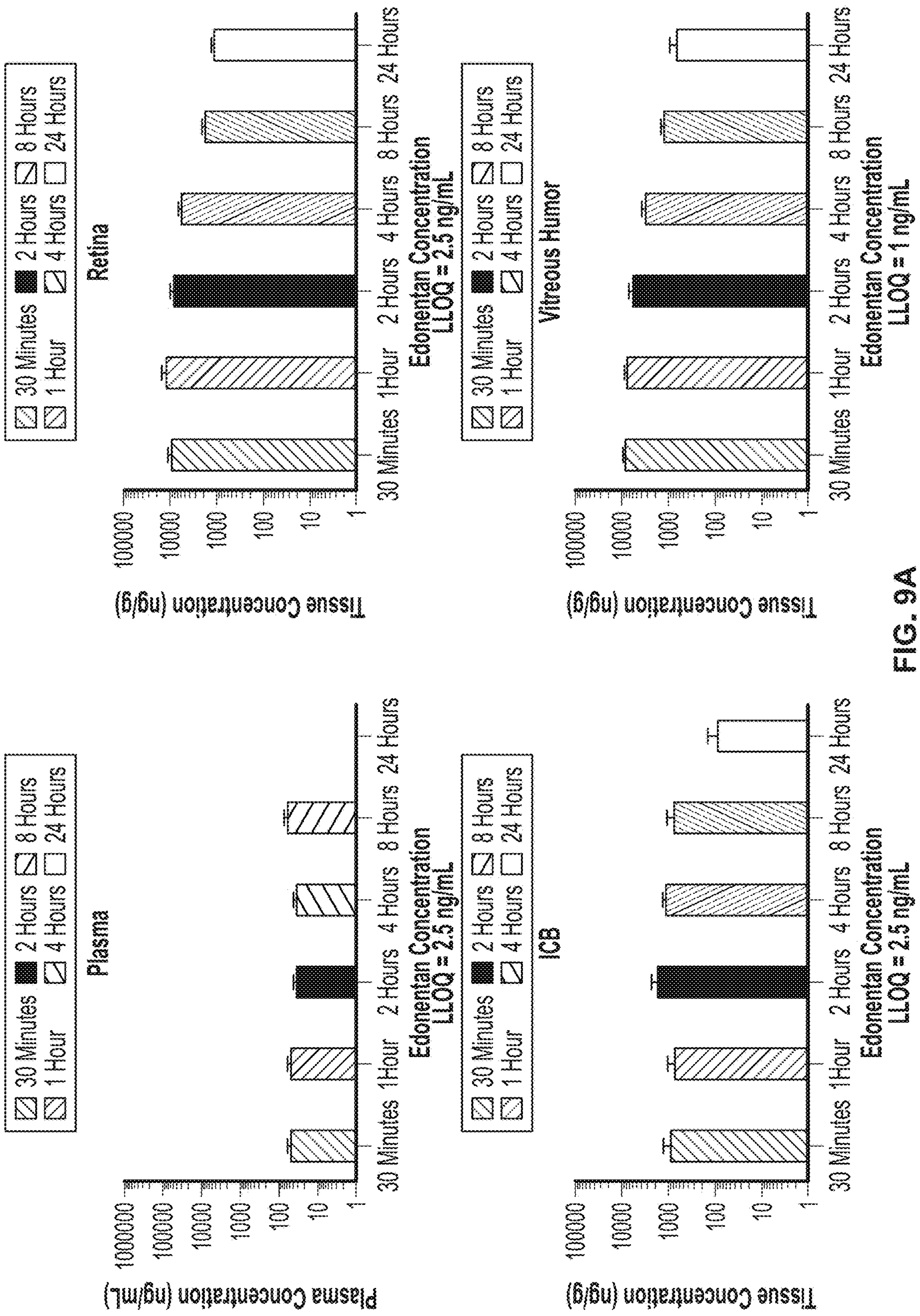
FIG. 9A, FIG. 9B, FIG. 9C and FIG. 9D depict pharmacokinetic profiles of intravitreally delivered Edonentan in the plasma, retina, iris-ciliary body (ICB), retinal pigment epithelium (RPE)/choroid, vitreous humor or aqueous humor of rabbits (FIG. 9A, FIG. 9B, FIG. 9C and FIG. 9D)—revealing longer tin for Edonentan.
Figure 9B:
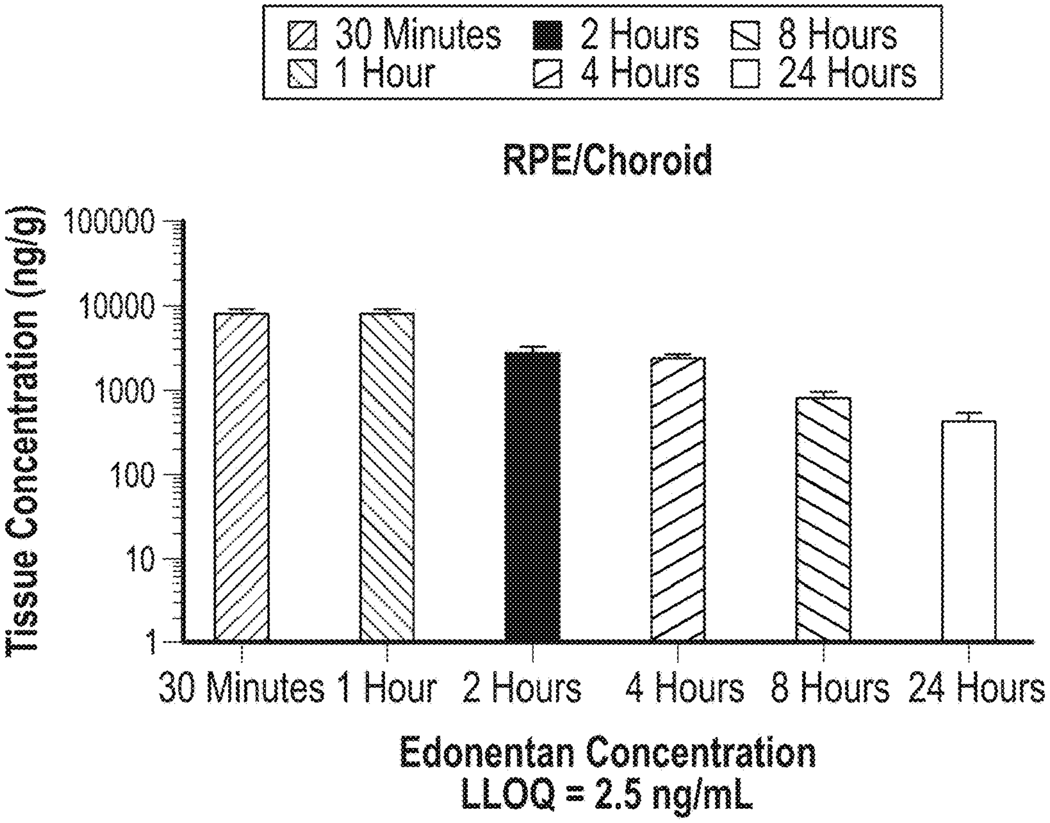
Figure 9B:
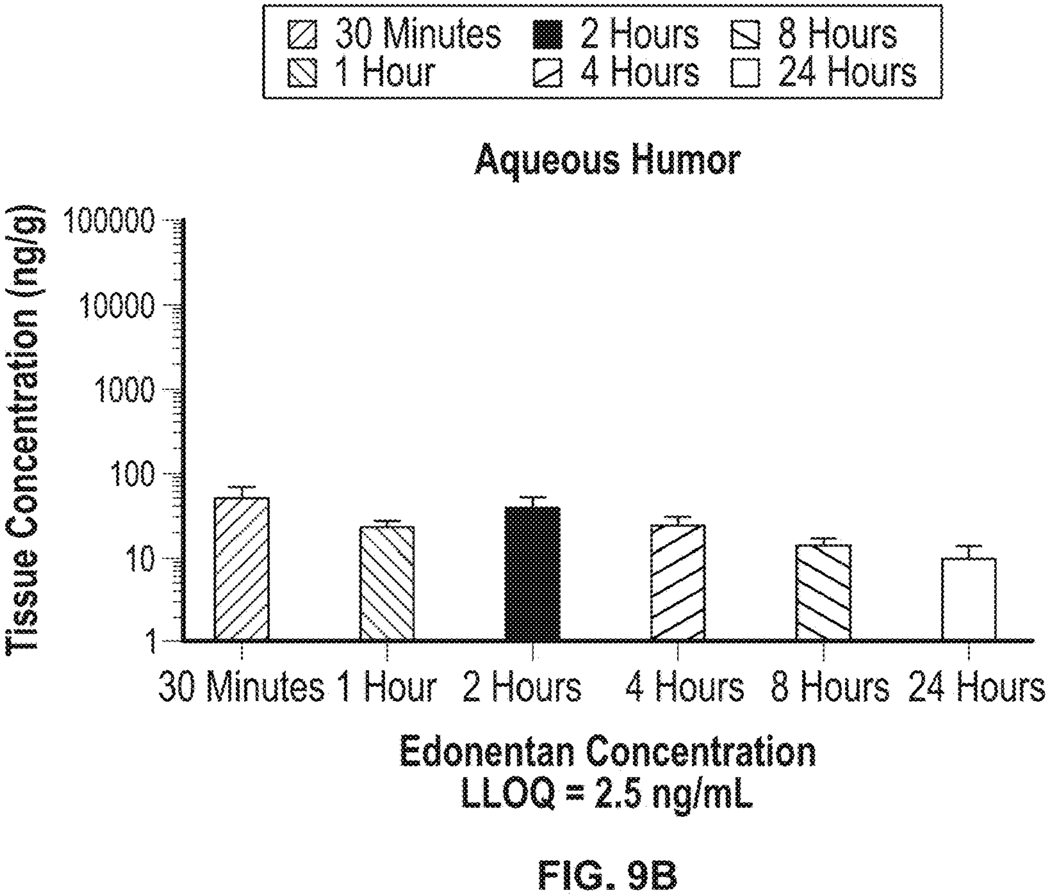
Figure 9C:
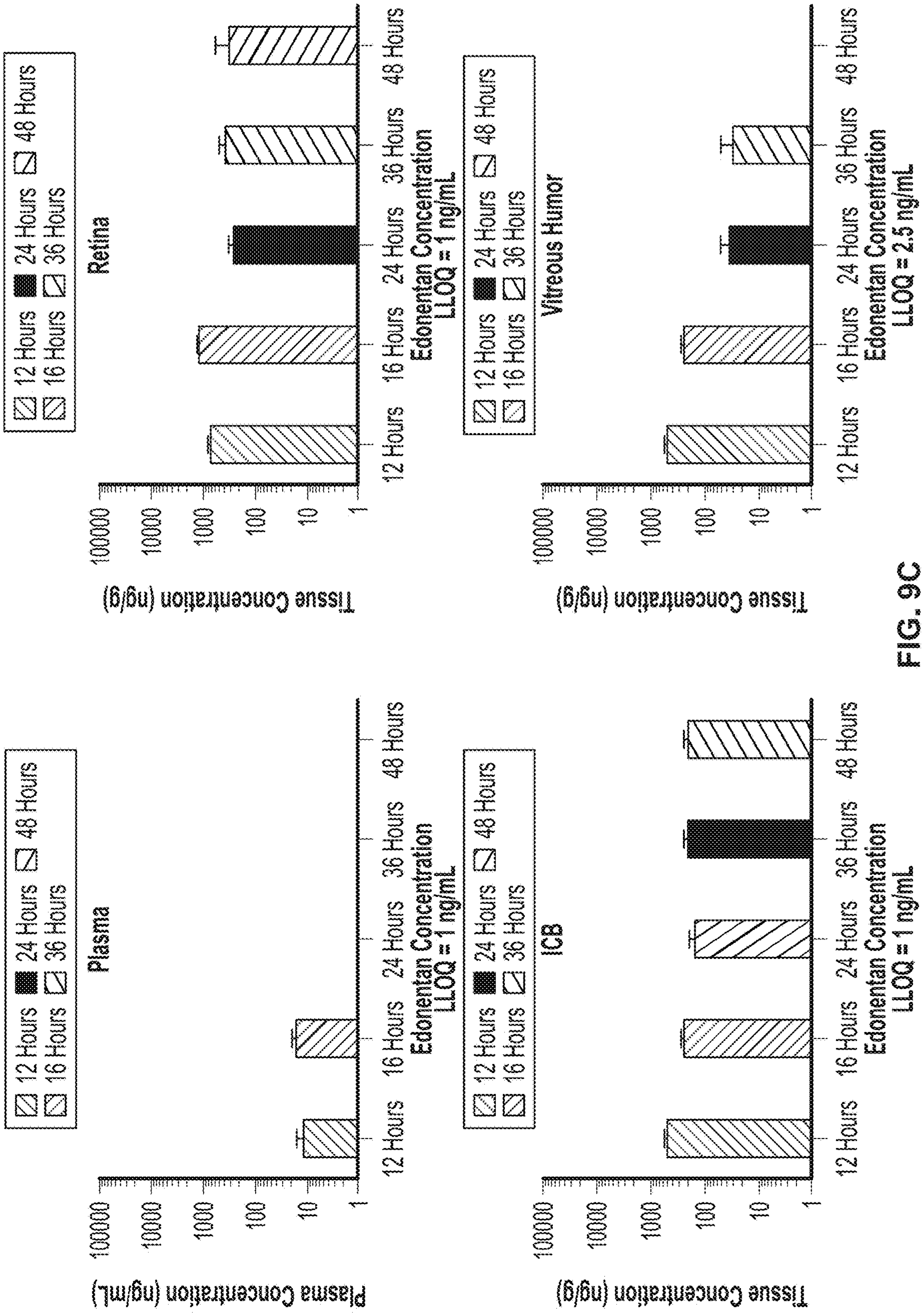
Figure 9D:
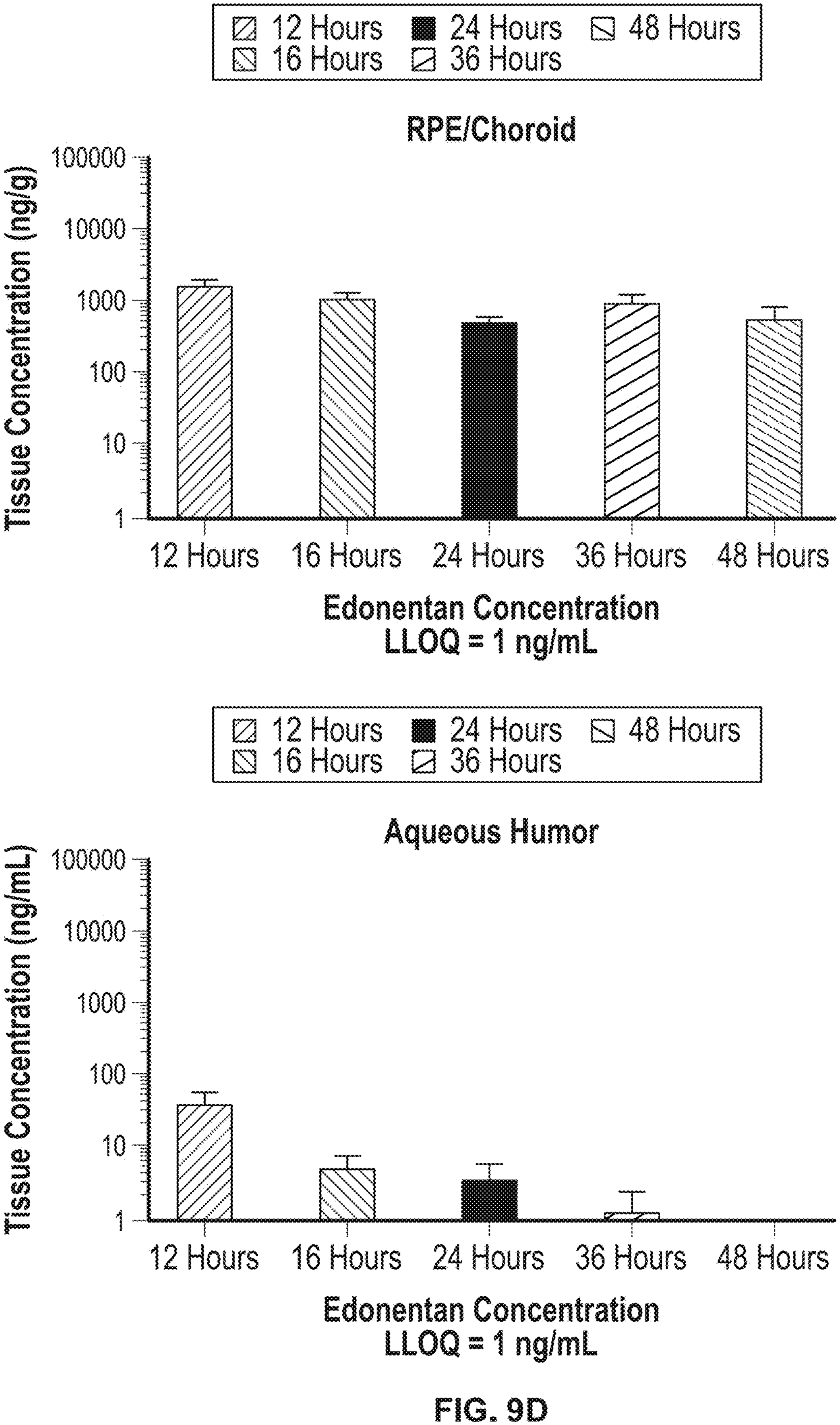

To evaluate the effect of retinal blood flow following intravitreally administered endothelin-1 (ET-1) followed by the antagonist Edonentan in the rabbit, rabbits (*Oryctolagus cuniculus*) were given a 20 µL intravitreal injection of ET-1 in the left eye followed by a 20 µL intravitreal injection of Edonentan at 2 (or 3) different doses (e.g. 0.1 µg. 0.5 µg. 2.5 µg). The pulse ox, tonometry, optical coherence tomography angiography (OCTA), fluorescein angiography (FA) and retinal leakage scoring were performed for evaluation. The dose-response in the rabbit is shown in FIG. 8A and FIG. 8B.

Pharmacokinetic and Tolerability Analysis of Edonentan Delivered Intravitreally in the Rabbit To determine the pharmacokinetic and safety properties of Edonentan following intravitreal administration in the rabbit, rabbits (*Oryctolagus cuniculus*) received bilateral intravitreal injections (20 μL injection volume/eye). Following the injections, animals were tranquilized with a ketamine/xylazine cocktail, and then the animals were euthanized with an overdose of sodium pentobarbital (Euthasol). Animals designated for the pharmacokinetic analysis were euthanized at different time points (e.g. 12, 16, 24, 36 and 48 hours). At least 1.0 mL of whole blood was drawn from the marginal ear vein or cardiac puncture (terminal bleed only) into $K_2$EDTA tubes for plasma collection and processed for analytical analysis.

Immediately following euthanasia, the eyes was enucleated. Aqueous humor from both eyes was removed via syringe and snap frozen for analysis. Eyes were dissected when frozen to isolate various ocular tissues and minimize drug diffusion to adjacent tissues. Tissues from left and right eyes were collected in separate vials for analysis. List of tissues collected include plasma and aqueous humor, iris/ciliary body (ICB), retina, vitreous humor and RPE/choroid. The pharmacokinetic properties of intravitreally delivered Edonentan in rabbits are shown in FIG. 9A, FIG. 9B, FIG. 9C and FIG. 9D.

Pharmacokinetic Analysis of Edonentan Administered Topically in the Rabbit

Figure 10:
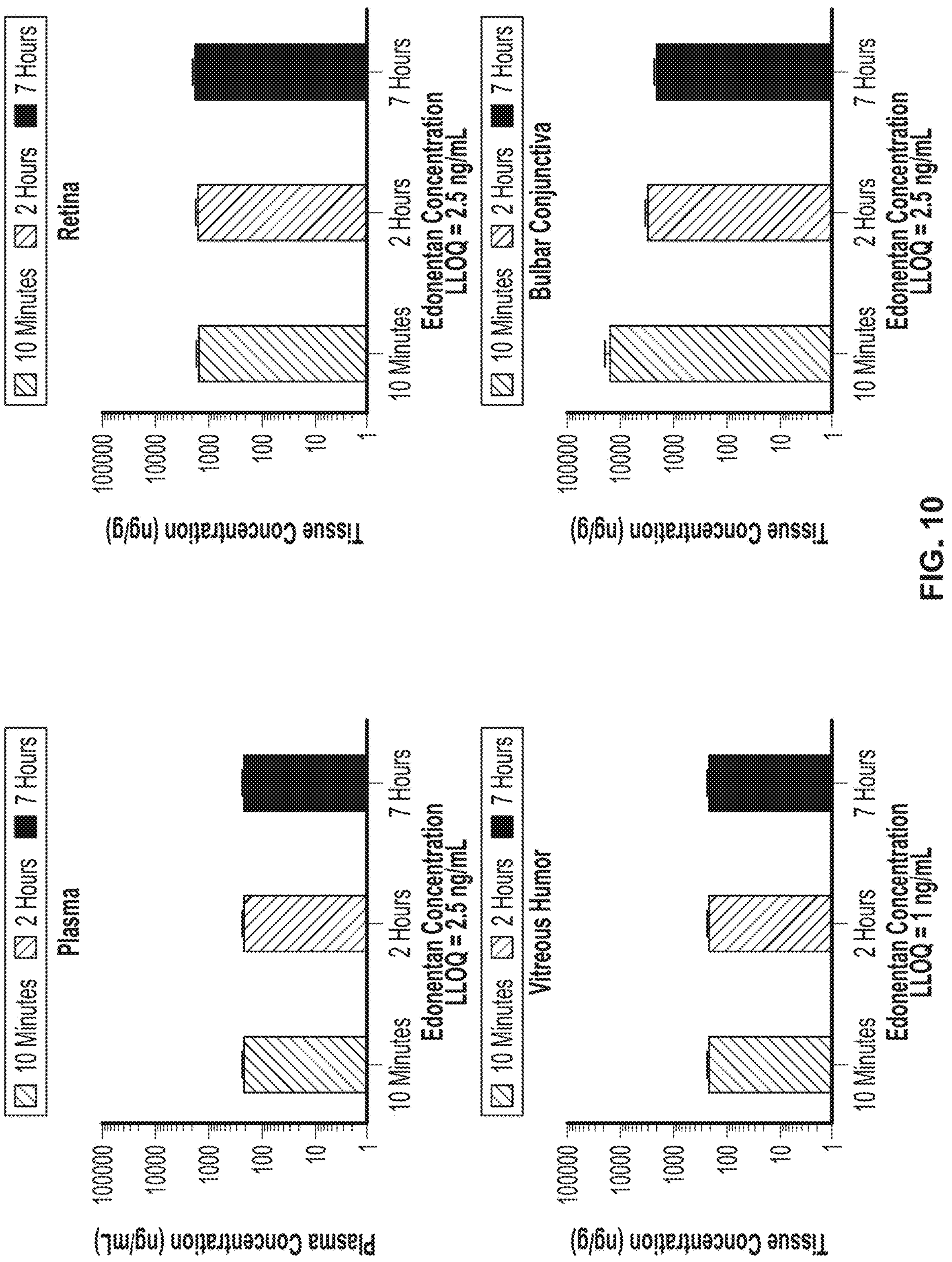
FIG. 10 depicts pharmacokinetic profiles of topically administered Edonentan in the plasma, retina, vitreous humor and bulbar conjunctiva of rabbits—revealing the ability of Edonentan to penetrate through ocular layers after a single topical application to the eye.

To determine the pharmacokinetic properties of Edonentan following topical administration in the rabbit, rabbits (Dutch-belted rabbits) received an eye drop in both eyes (100 μg of Edonentan, 35 μL dose volume/eye). After the administrations, the animals (N=2) were euthanized at different time points (e.g. 10 minutes (immediately after pot-dose), 2 and 7 hours) and tissues were collected for analysis. List of tissues collected include plasma, retina, vitreous humor and bulbar conjunctiva. The pharmacokinetic properties of topically delivered Edonentan in rabbits are shown in FIG. 10, which shows that Edonentan was detected in all tissues examined at all timepoints after a single topical application.

Efficacy Study in the Morrison's Rat Model of Glaucoma

Adult male and female retired breeder Brown Norway rats (approximate age groups of 8 to 11 months) were obtained from Envigo (Indianapolis. IN). Baseline IOP measurements and pattern electroretinogram (PERG) amplitudes were collected prior to the surgery for elevation of IOP (to ensure that the IOP and PERG amplitudes were in the expected range of values). IOP was elevated in one eye (left eye) of the rats, while the corresponding right eyes served as contralateral controls. The Morrison method to elevate IOP in rats was carried out by injection of 50 μL of hypertonic saline through the episcleral veins to sclerose the trabecular meshwork. IOP was measured twice a week throughout the entire duration of the experiment. Seven to ten days following the surgery. IOP elevation was observed in the operated eye of rats. After detecting an elevation of IOP for two consecutive days, topical administration of eye drops (20 μL (100 μg) per dose of the tested compounds in the IOP elevated eye) was commenced and carried out for five days a week for a total of four weeks. In the 4th week of treatment, PERG analysis was carried out and rats were sacrificed by an overdose of pentobarbital (Fatal-Plus). Aqueous humor was collected from the rat eyes, frozen and shipped for analysis. Retinal flat mounts were prepared, immunostained with the RGC marker, Brn3a antibody and surviving RGCs were counted in two eccentricities (central and peripheral).

For this study, the Morrison's model was used to induce ocular hypertension in adult male retired breeder Brown Norway rats as previously described by Morrison et al., (Morrison J C, Moore C G, Deppmeier L M, Gold B G, Meshul C K, Johnson E C. *A rat model of chronic pressure-induced optic nerve damage*. Exp Eye Res. 1997; 64(1):85-96).

Figure 5A:
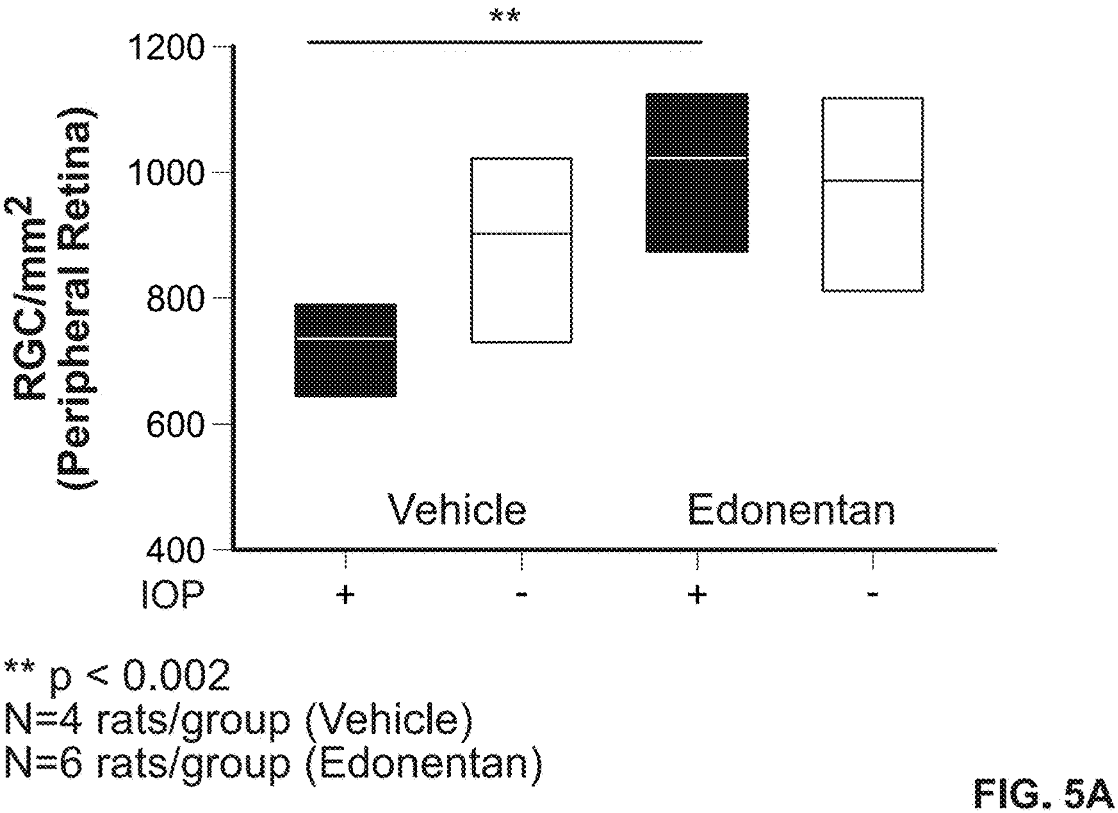
FIG. 5A depicts the comparison of retinal ganglion cell (RGC) counts in the peripheral retina of rats with elevated intraocular pressure (IOP) (n=4 rats/group for control, n=6 rats/group for Edonentan) after topical administration of vehicle alone (control group) or Edonentan.
Figure 6A:
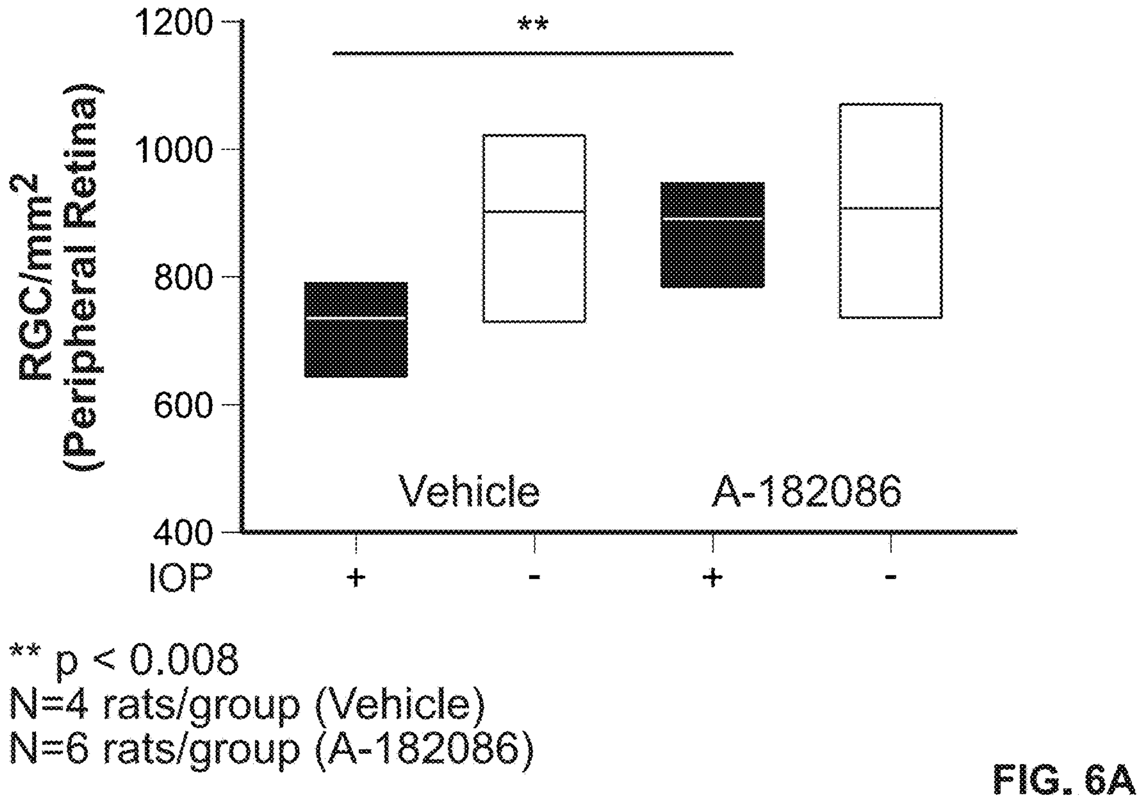
FIG. 6A depicts the comparison of retinal ganglion cell (RGC) counts in the peripheral retina of rats (n=4 rats/group for control, n=6 rats/group for A-182086) with elevated intraocular pressure (IOP) after topical administration of vehicle alone (control group) or A-182086.

The immunostained retinal flat mounts were obtained to measure the retinal ganglion cell (RGC) counts. To obtain immunostained retinal flat mounts, the animals were euthanized after the treatments and then their eyes were enucleated. The eye cups were fixed overnight at 4° C. in 4% paraformaldehyde (PFA) and retinal flat mounts were prepared for collecting images. The retinal ganglion cell (RGC) counting was conducted using the images of immunostained retinal flat mounts. The images were uploaded to ImageJ, a photo editor designed for biology research (Rasband, 1997-2018) and the labeled retinal ganglion cells were counted manually in two eccentricities (central and peripheral). FIG. 5A shows the comparison of RGC counts in the peripheral retinal between vehicle and Edonentan, and FIG. 6A shows the comparison between vehicle and A-182086.

Figure 5B:
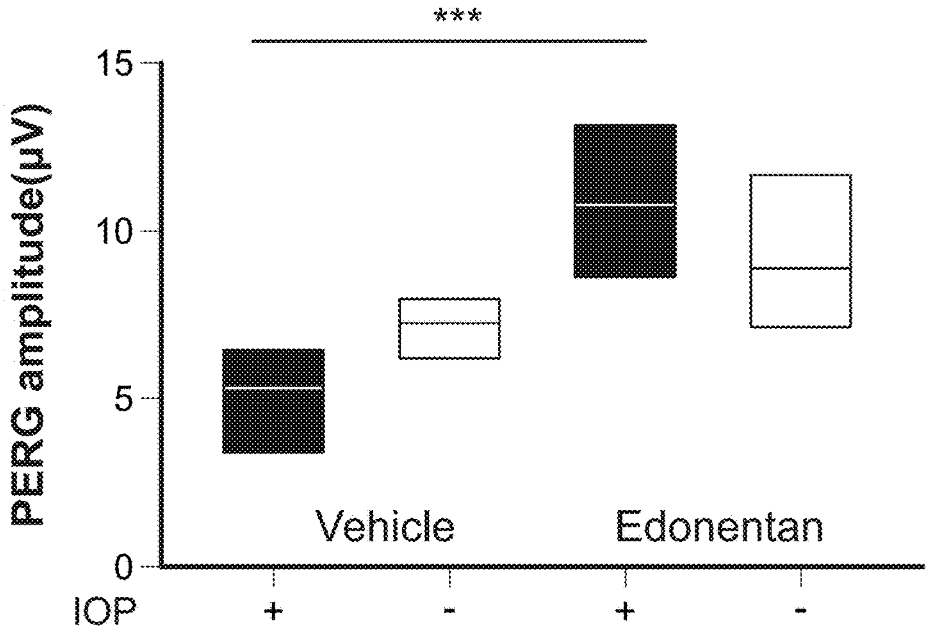
FIG. 5B depicts the comparison of pattern electroretinogram (PERG) changes in with elevated intraocular pressure (IOP) rats (n=4 rats/group for control, n=5 rats/group for Edonentan) after topical administration of vehicle alone (control group) or Edonentan.
Figure 6B:
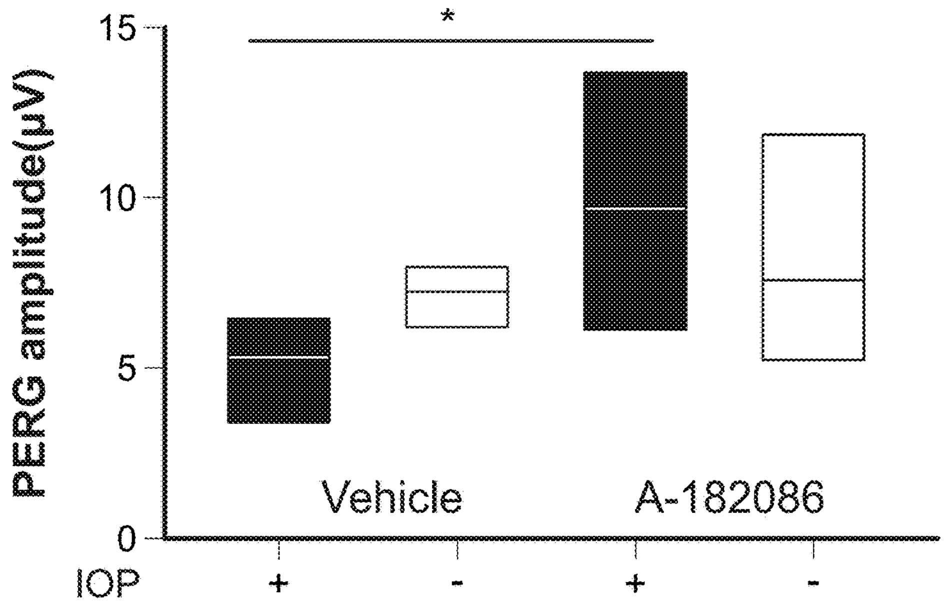
FIG. 6B depicts the comparison of pattern electroretinogram (PERG) changes in rats (n=4 rats/group for control, n=5 rats/group for A-182086) with elevated intraocular pressure (IOP) after topical administration of vehicle alone (control group) or A-182086.

Pattern ERG (PERG) was used to assess the RGC function. To obtain the pattern erg recordings, a UTAS Visual Electrodiagnostic System (LKC, Gaithersburgh, MD, USA) was used following the method described by Porciatti et al. (Porciatti V, Saleh M, Nagaraju M. The pattern electroretinogram as a tool to monitor progressive retinal ganglion cell dysfunction in the DBA/2J mouse model of glaucoma. *Invest Ophthalmol Vis Sci.* 2007; 48(2):745-751). Briefly. PERG signals were acquired from a DTL-plus electrode placed on the lower part of the corneal surface and the PERG waves were analyzed using the EMWIN software (LKC). The difference between the amplitude of the major positive (P1) and negative (N2) waves were calculated to deciper the PERG amplitude. FIG. 5B shows IOP-mediated PERG changes between vehicle and Edonentan, and FIG. 6B shows the changes between vehicle and A-182086.

The RGC counts and PERG changes reveal that both Edonentan and A-182086 prevented RGC loss and maintained RGC function in the morrison's rat model of glaucoma, as shown in FIG. 5A, FIG. 5B, FIG. 6A and FIG. 6B.

Figure 5C:
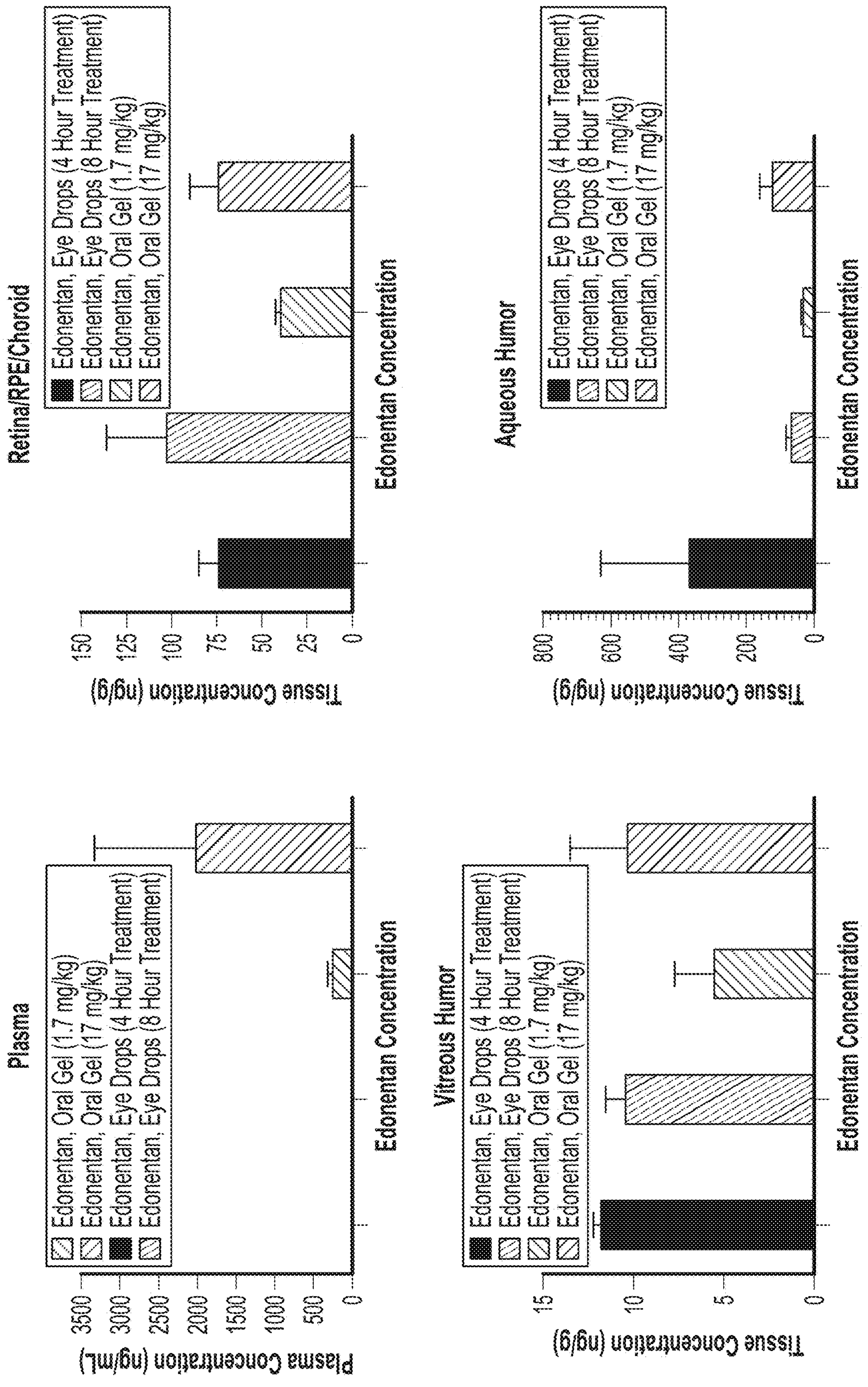
FIG. 5C depicts pharmacokinetic profiles of topically or orally administered Edonentan in the plasma, retina/retinal pigment epithelium (RPE)/choroid, vitreous humor and aqueous humor of rats.
Figure 6C:
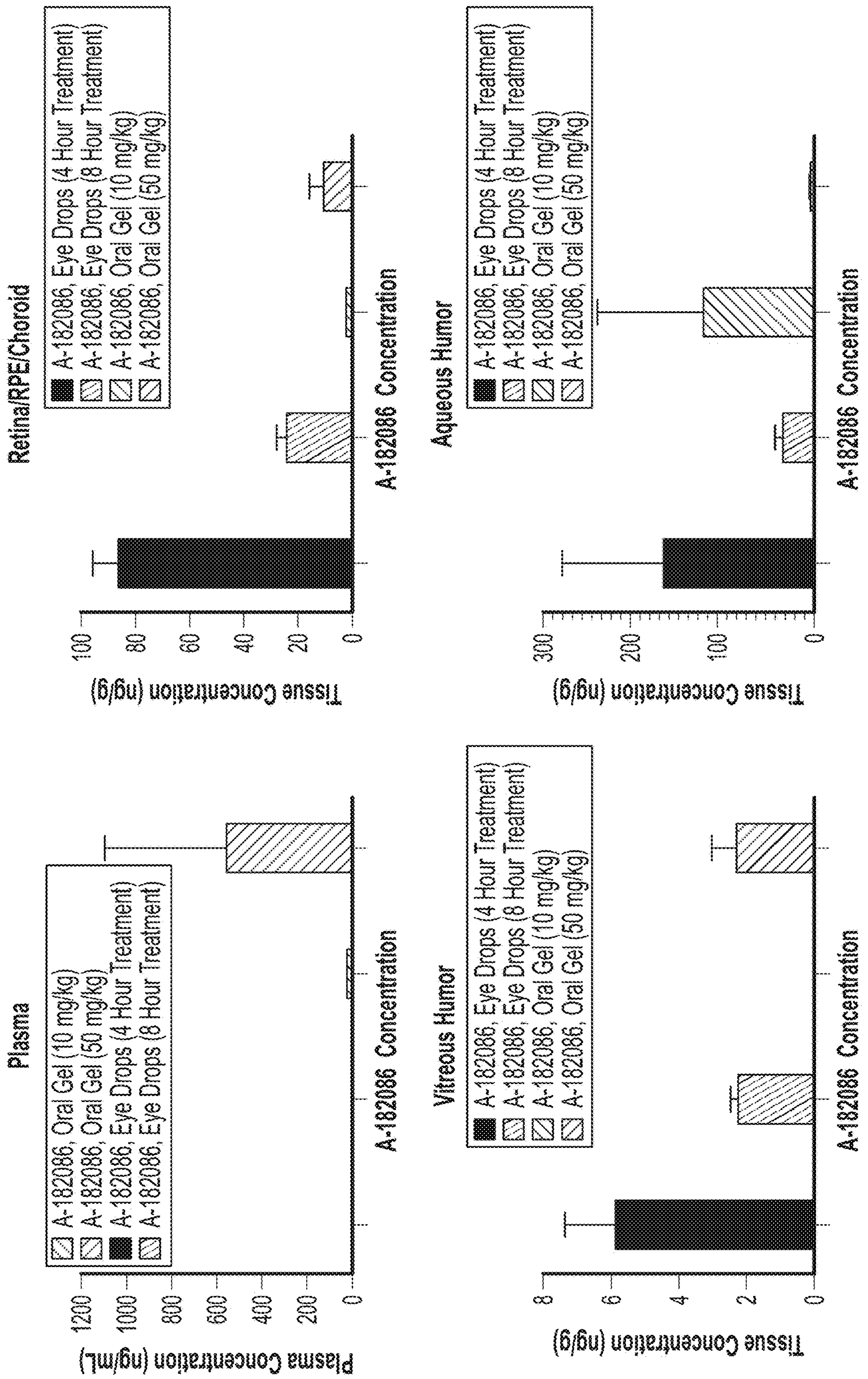
FIG. 6C depicts pharmacokinetic profiles of topically or orally administered A-182086 in the plasma, retina/retinal pigment epithelium (RPE)/choroid, vitreous humor and aqueous humor of rats.

Pharmacokinetic Analysis of Edonentan or A-182086 Delivered Topically or Orally in the Rat To determine the pharmacokinetic properties of Edonentan or A-182086 following topical administration in the rat, rats (Brown Norway rats) received an eye drop (100 μg of Edonentan, 20 μL dose volume/eye; or 100 μg of A-182086, 20 μL dose volume/eye). To determine the pharmacokinetic properties of Edonentan or A-182086 following oral administration in the rat, rats (Brown Norway rats) received an oral administration of 10 mg/kg or 50 mg/kg of Edonentan, or an oral administration of 1.7 mg/kg or 17 mg/kg of A-182086. After the administrations, the animals (N=2) were euthanized at different time points (e.g. 4 and 8 hours) and tissues were collected for analysis. List of tissues collected include plasma, retina/retinal pigment epithelium (RPE)/choroid, vitreous humor and aqueous humor. The pharmacokinetic properties of topically or orally administered Edonentan in rats is shown in FIG. 5C. The pharmacokinetic properties of topically or orally administered A-182086 in rats is shown in FIG. 6C. FIG. 5C and FIG. 6C show that both Edonentan and A-182086 are detected 4 and 8 hours post-topical administration in the retina/RPE/choroid, aqueous humor and vitreous humor. These data also revealed that Edonentan was detectable in the aqueous humor at the 17 mg/kg and in the retina/RPE/choroid and vitreous humor at 1.7 and 17 mg/kg, after oral administration of Edonentan, and A-182086 was detectable in the retina/RPE/choroid at 50 mg/kg, after oral administration of A-182086.

Study in Mice with Oxygen-Induced Ischemic Retinopathy

Figure 4:
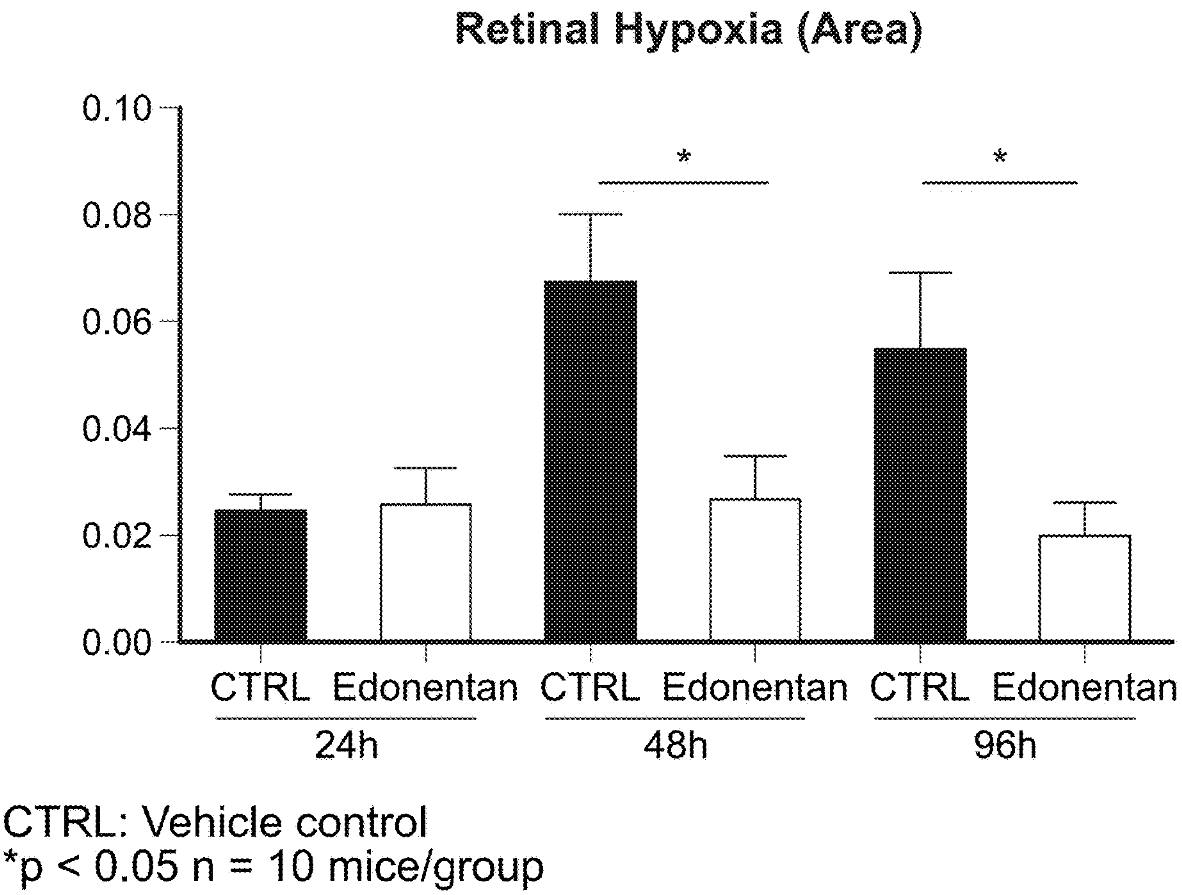
FIG. 4 depicts the comparison of retinal hypoxia area in mice (n=10 mice/group) with oxygen-induced ischemic retinopathy (OIR) at 24, 48, and 96 hours after IVT administration of vehicle alone (control group—DMSO) or a single dose of Edonentan (1 μL of 2 μg/μL solution)—revealing improved retinal hypoxia in mice with OIR after treatment with Edonentan.

A relevant mice model was used to obtain the retinal hypoxia area in mice with oxygen-induced ischemic retinopathy (OIR) at different time points, as shown in FIG. 4. The improvement of retinal hypoxia in the mouse oxygen-induced ischemic retinopathy (OIR) model by Edonentan is revealed. Briefly, at P17, mice with OIR (n=60) were given an injection of ET-1 antagonist (1 μL of 2 μg/μL Edonentan formulation, single dose) in one eye and PBS in the fellow eye. At 24, 48, and 96 hours after injection, mice (n=10 for each time point) were euthanized and the retinas were dissected and stained with GSA lectin and hypoxyprobe. The area of NV, area of retinal hypoxia, and the area of retinal nonperfusion were determined for each retina.

Example 8: Laser-Induced Non-Human Primate Studies—Pharmacodynamic Study

Non-human primates (rhesus macaque, *Macaca mulatta*) were obtained for this study. One eye of each animal underwent induction of elevation of intraocular pressure (IOP) by repeated laser photocoagulation of the trabecular meshwork. Imaging sessions were repeated to monitor the optic nerve head (ONH) and retinal structural changes.

Effect of Edonentan on Optic Nerve Head Blood Flow after IVT Administration

Figure 7A:
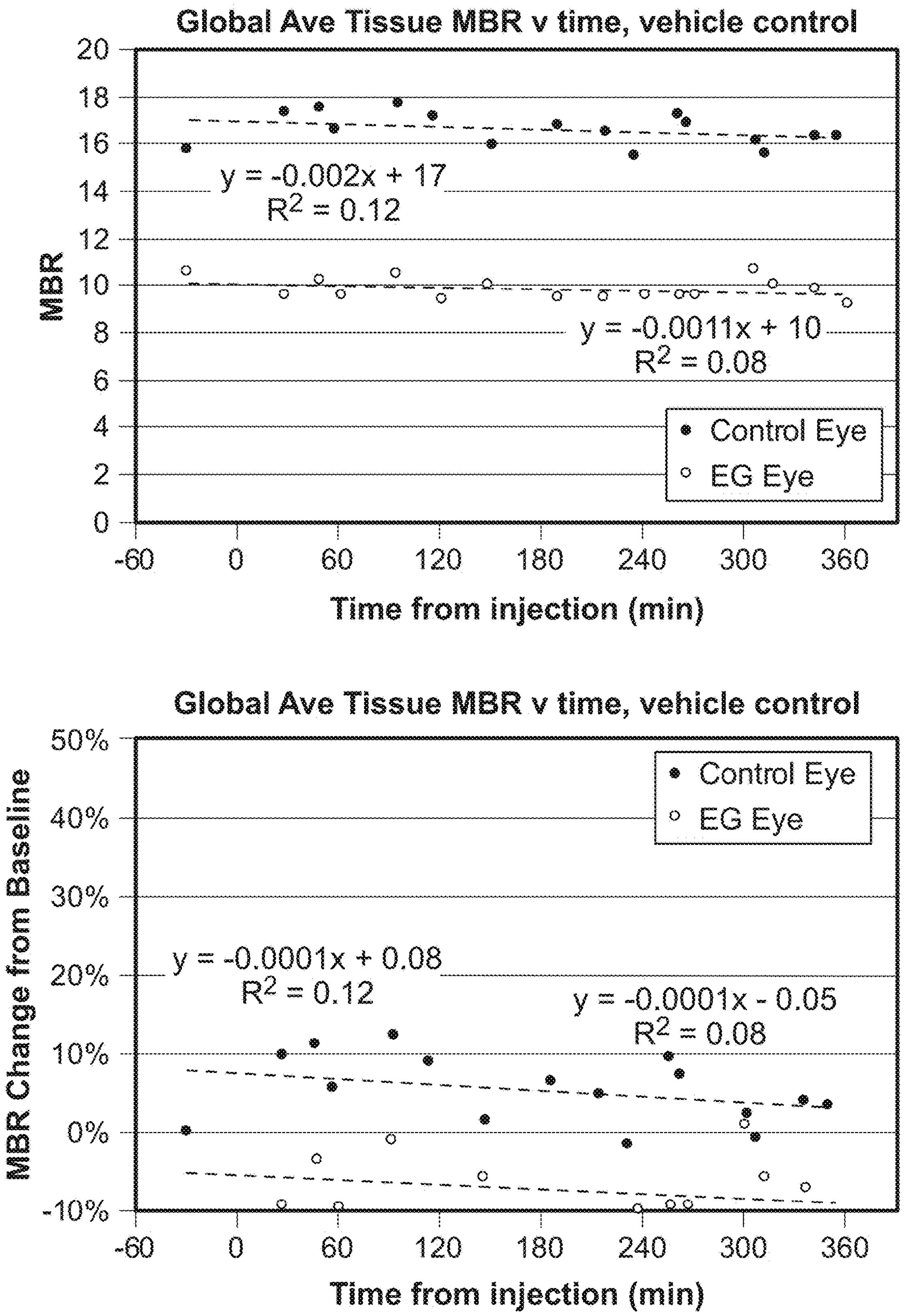
FIGS. 7A-7L depict laser speckle flow graphs (LSFG) for the comparison of an experimental glaucoma eye and a contralateral healthy eye (control) of three non-human primates in global average mean blur rate (MBR) or MBR change from baseline over time as an index of optic nerve head (ONH) blood flow in a laser-induced glaucoma model.
Figure 7B:
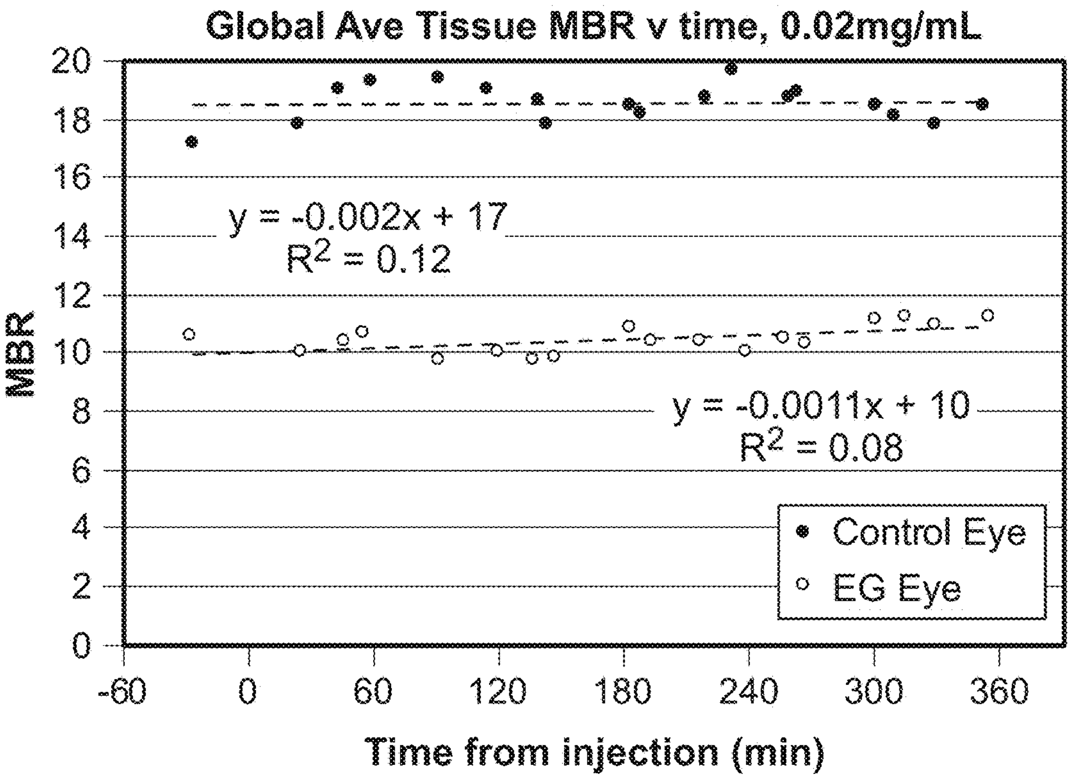
Figure 7B:
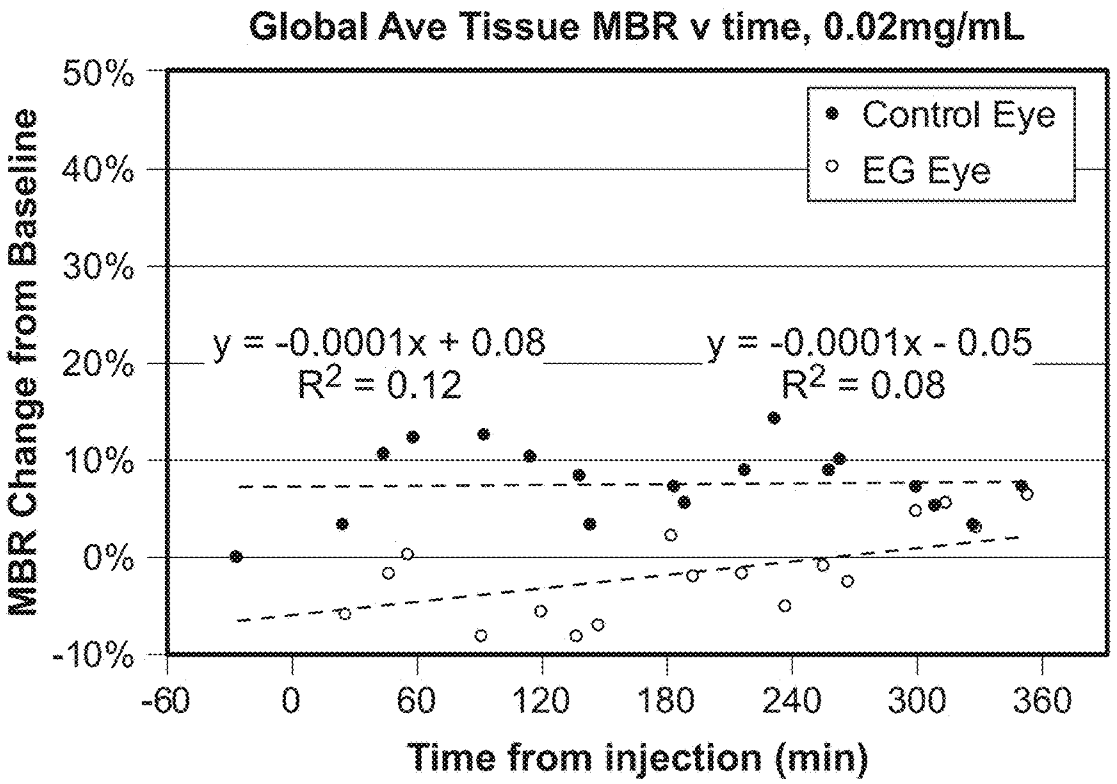
Figure 7C:
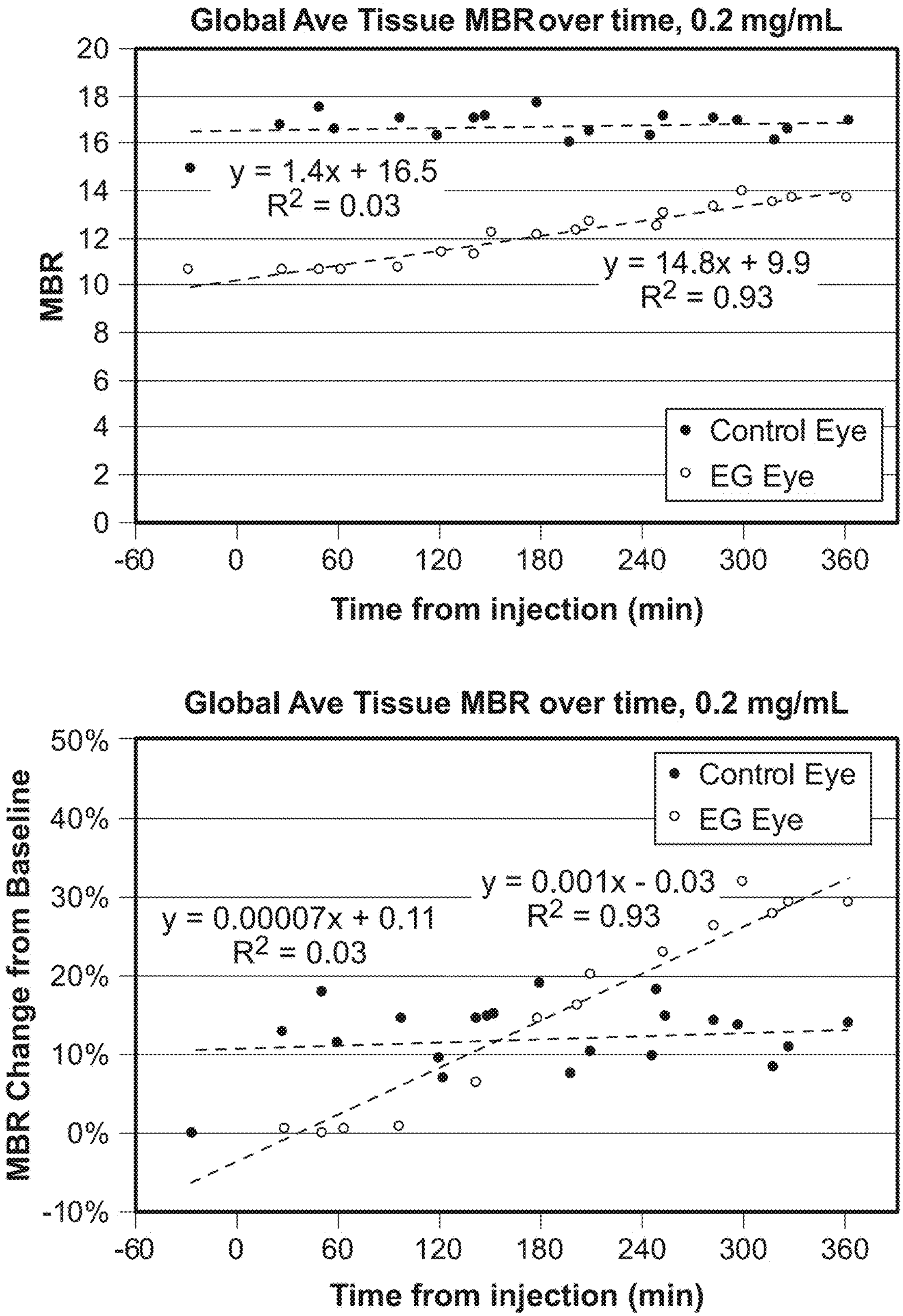
Figure 7D:
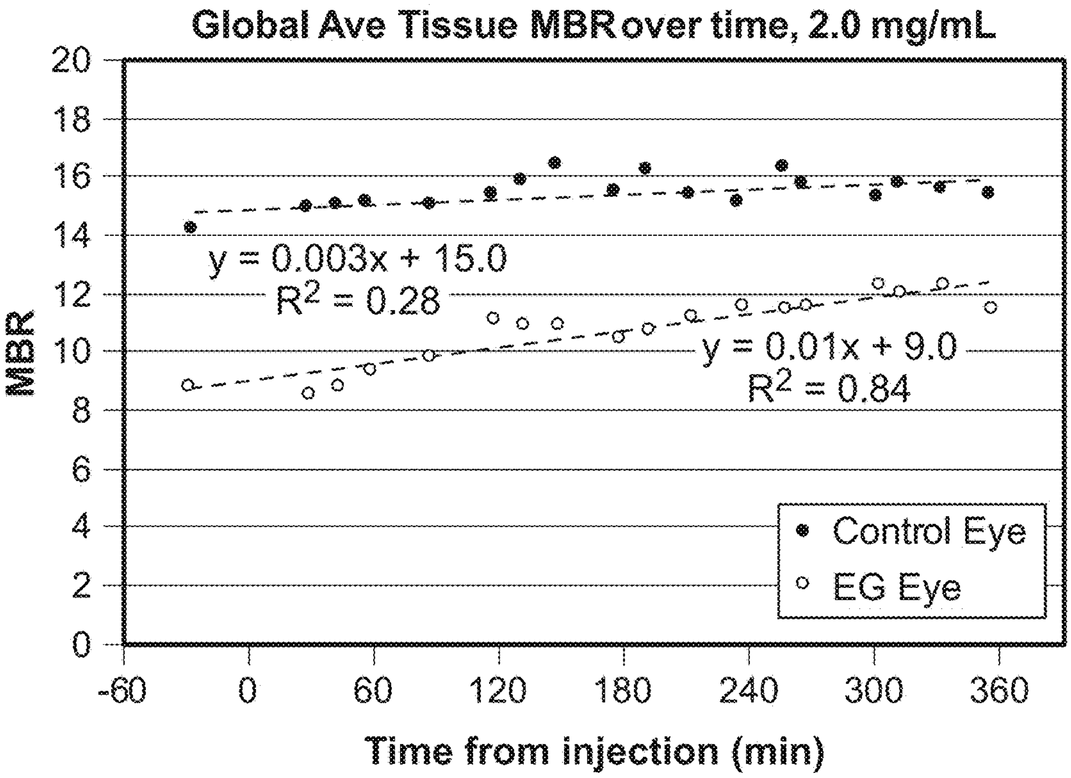
Figure 7D:
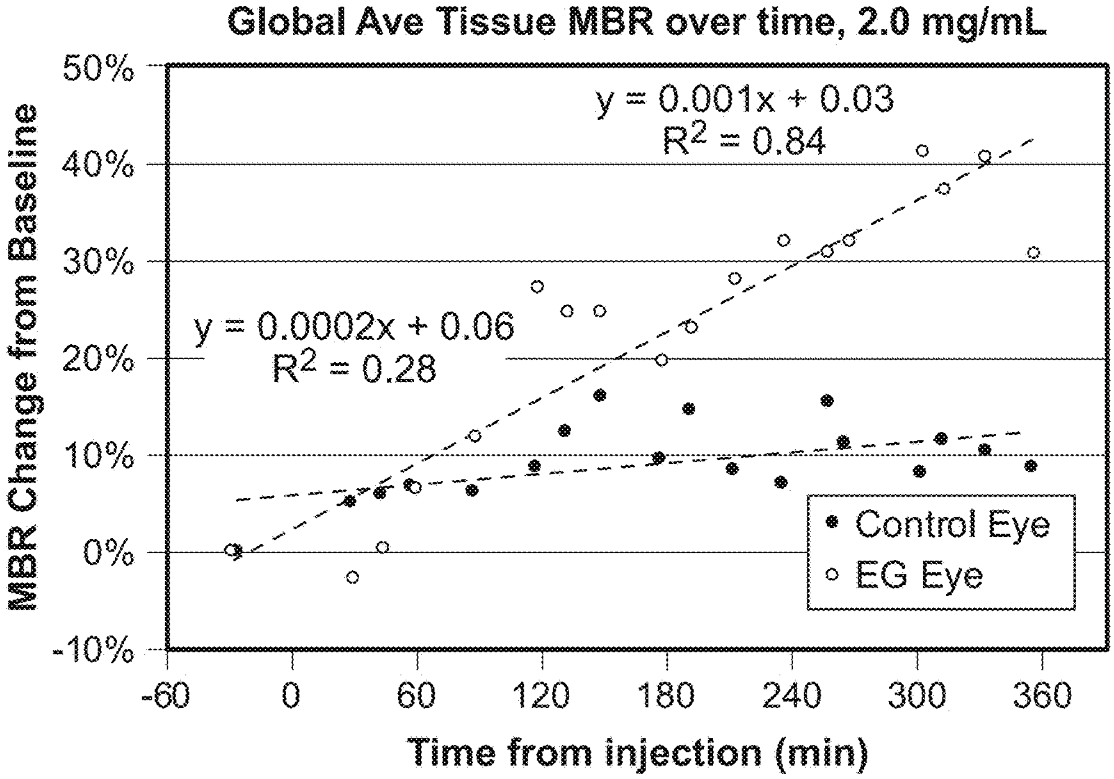
Figure 7E:
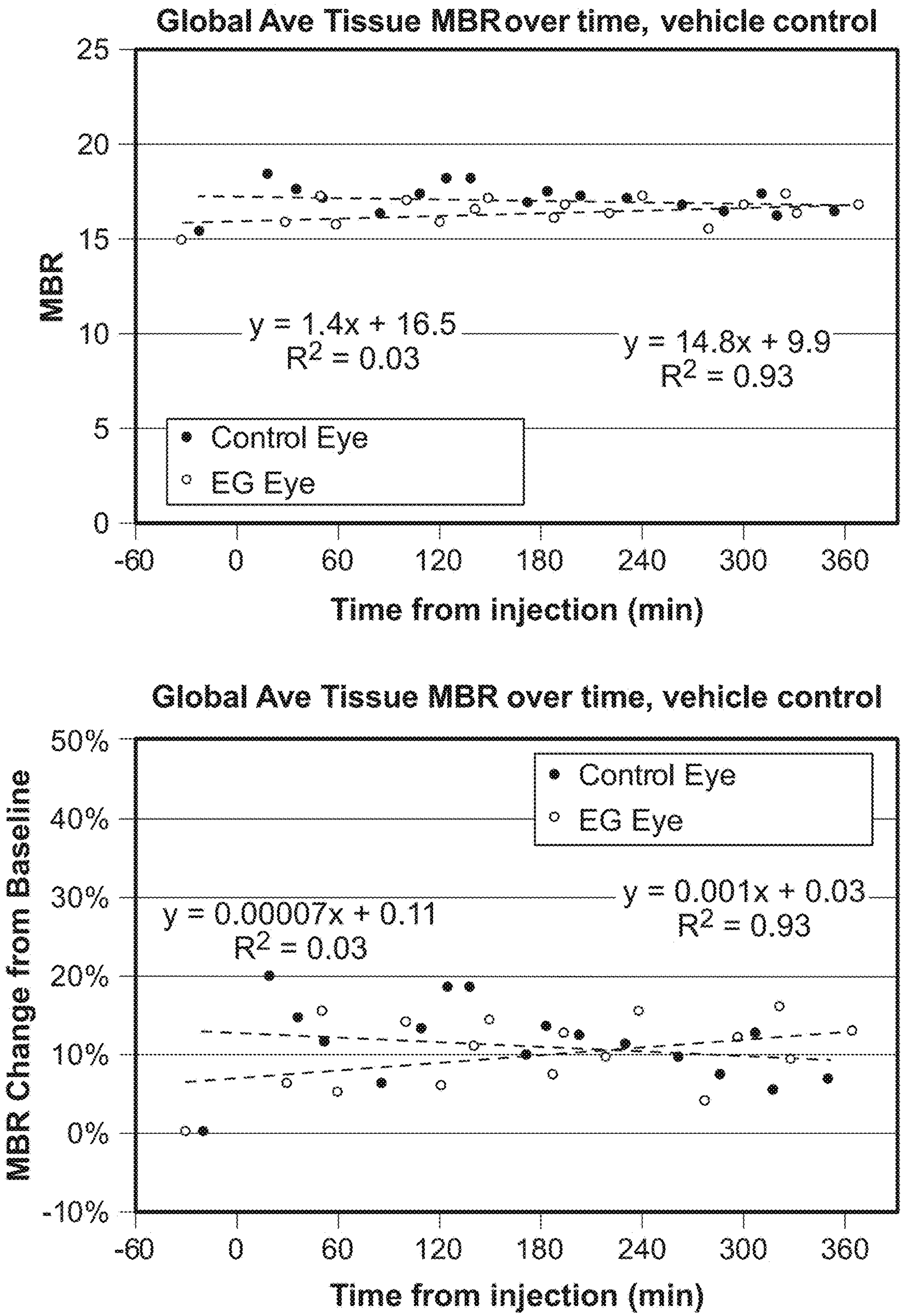
Figure 7F:
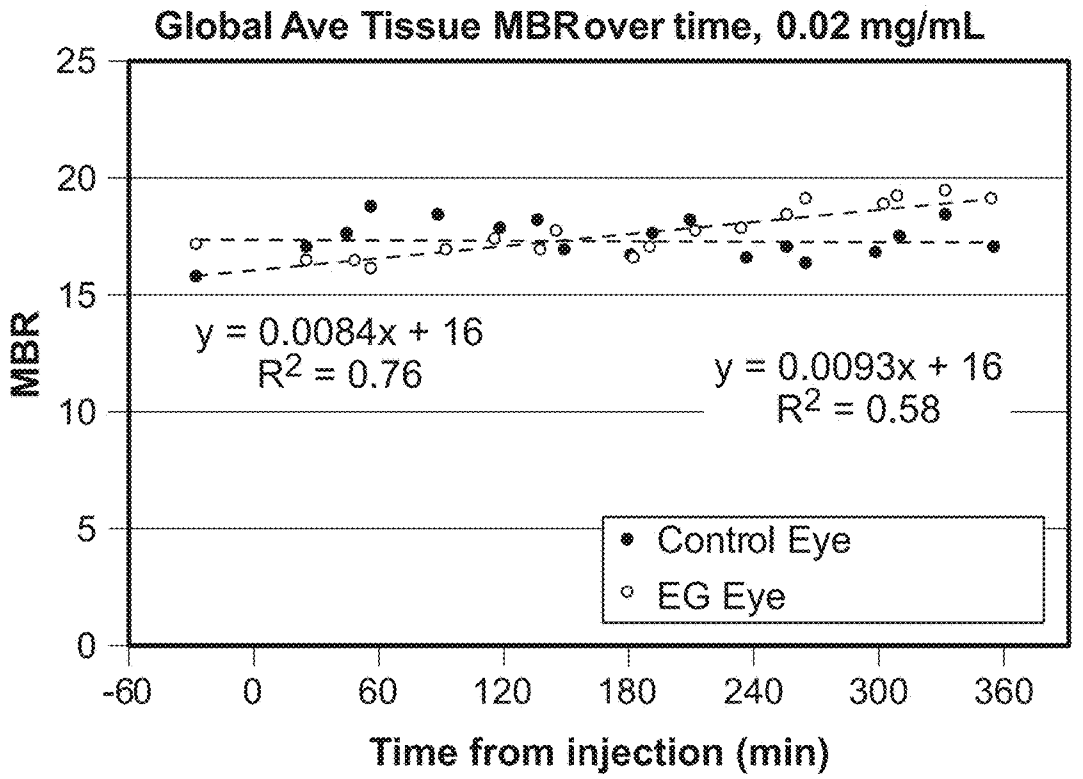
Figure 7F:
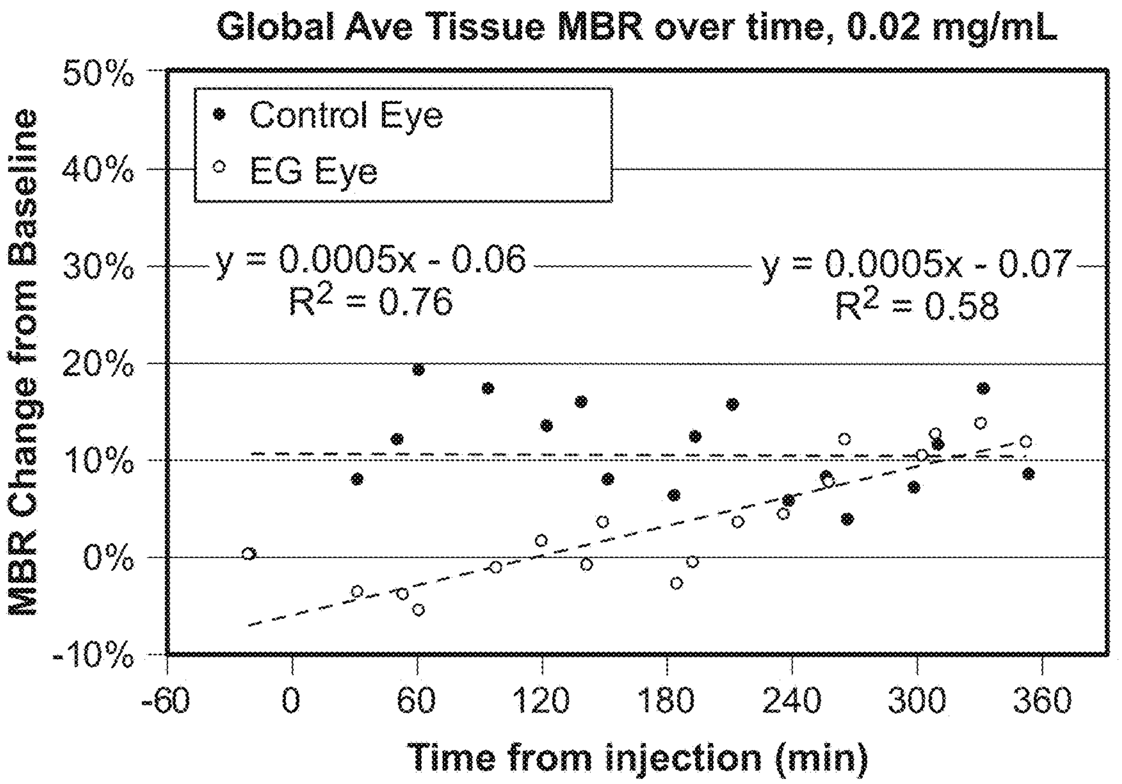
Figure 7G:
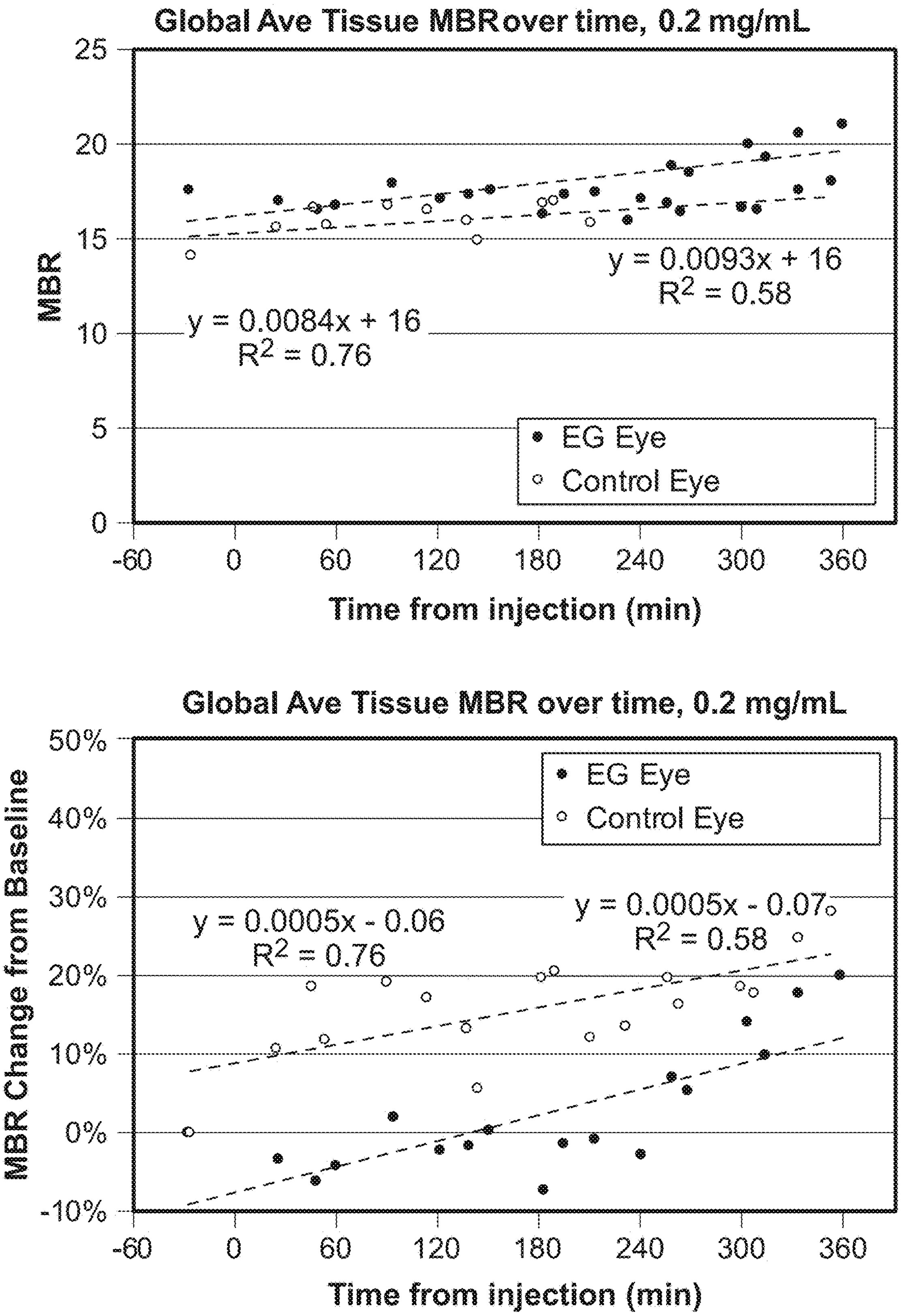
Figure 7H:
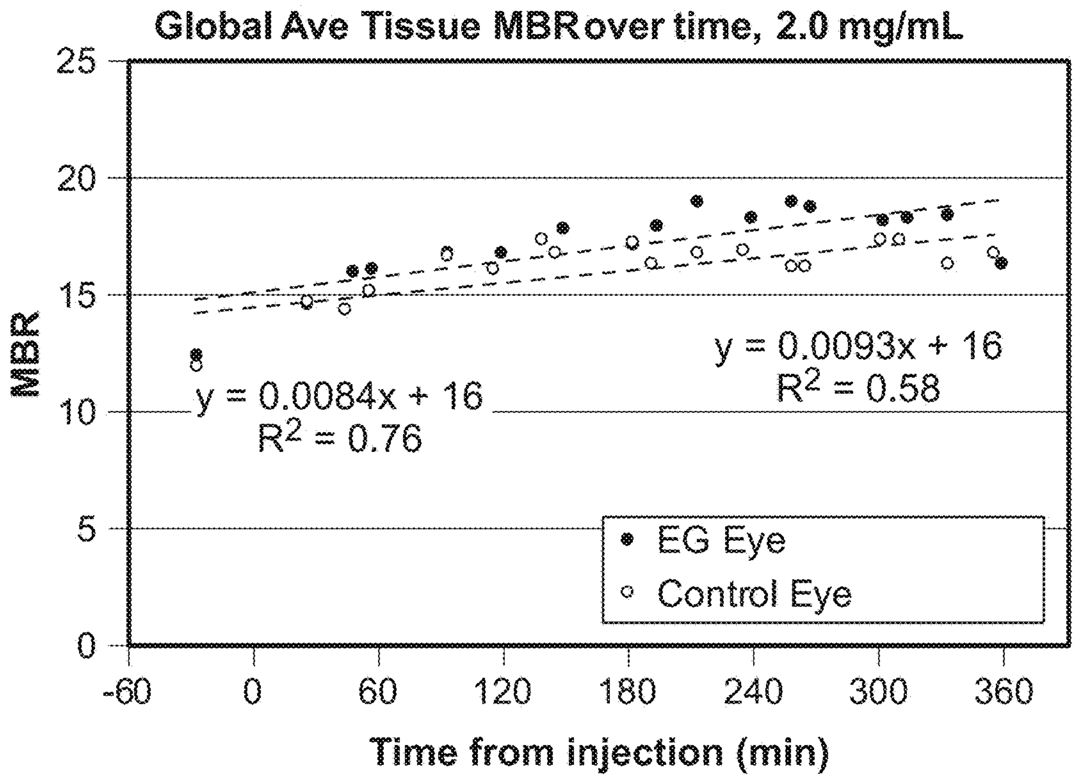
Figure 7H:
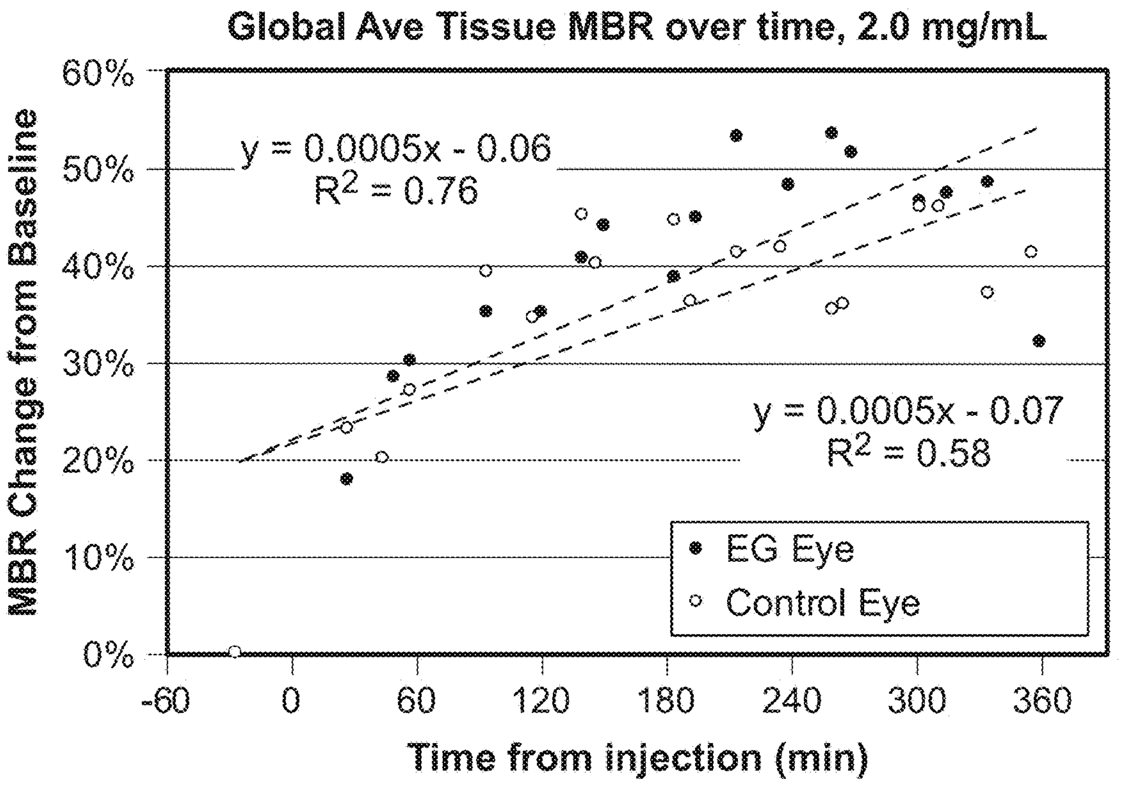
Figure 7I:
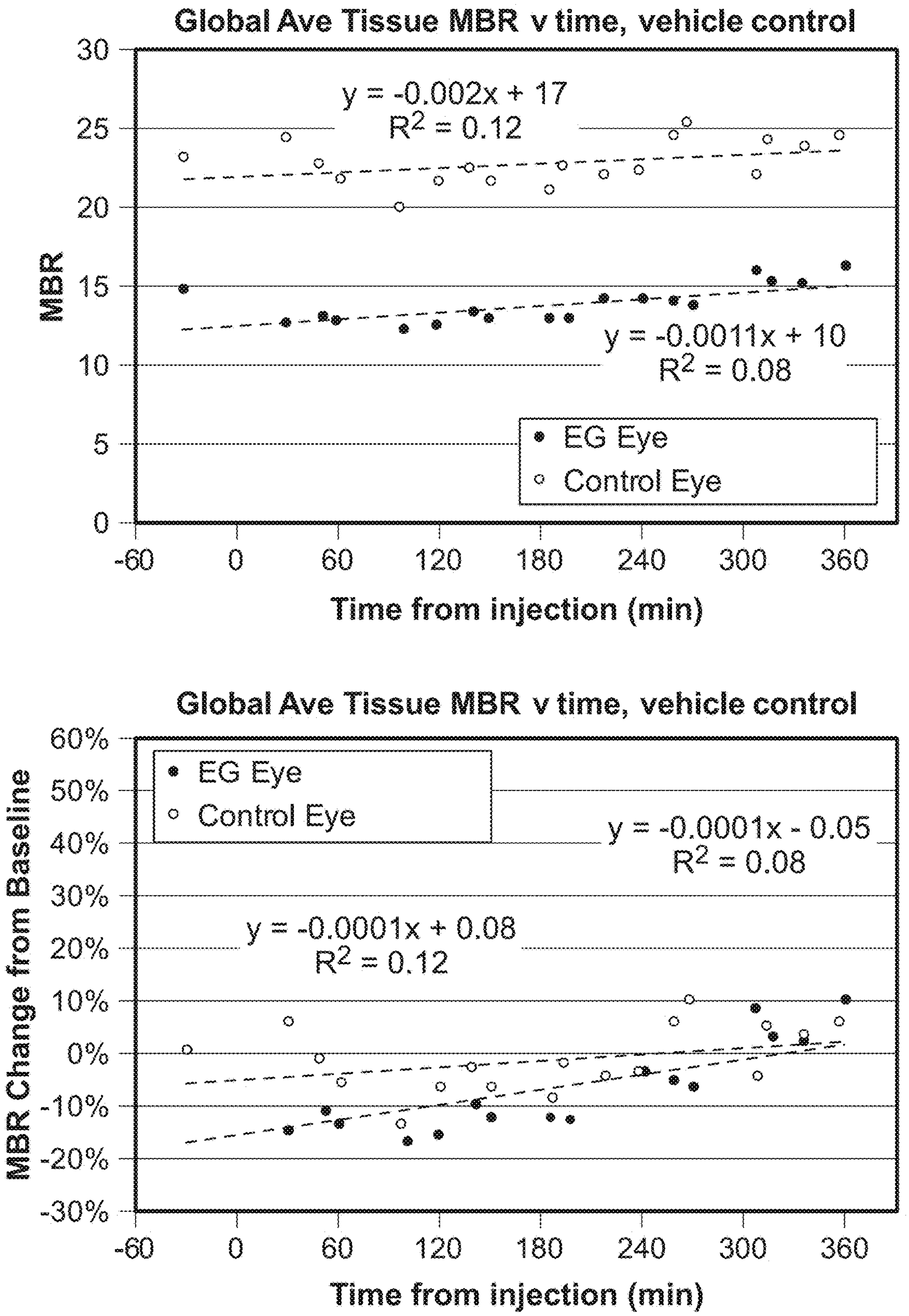
Figure 7J:
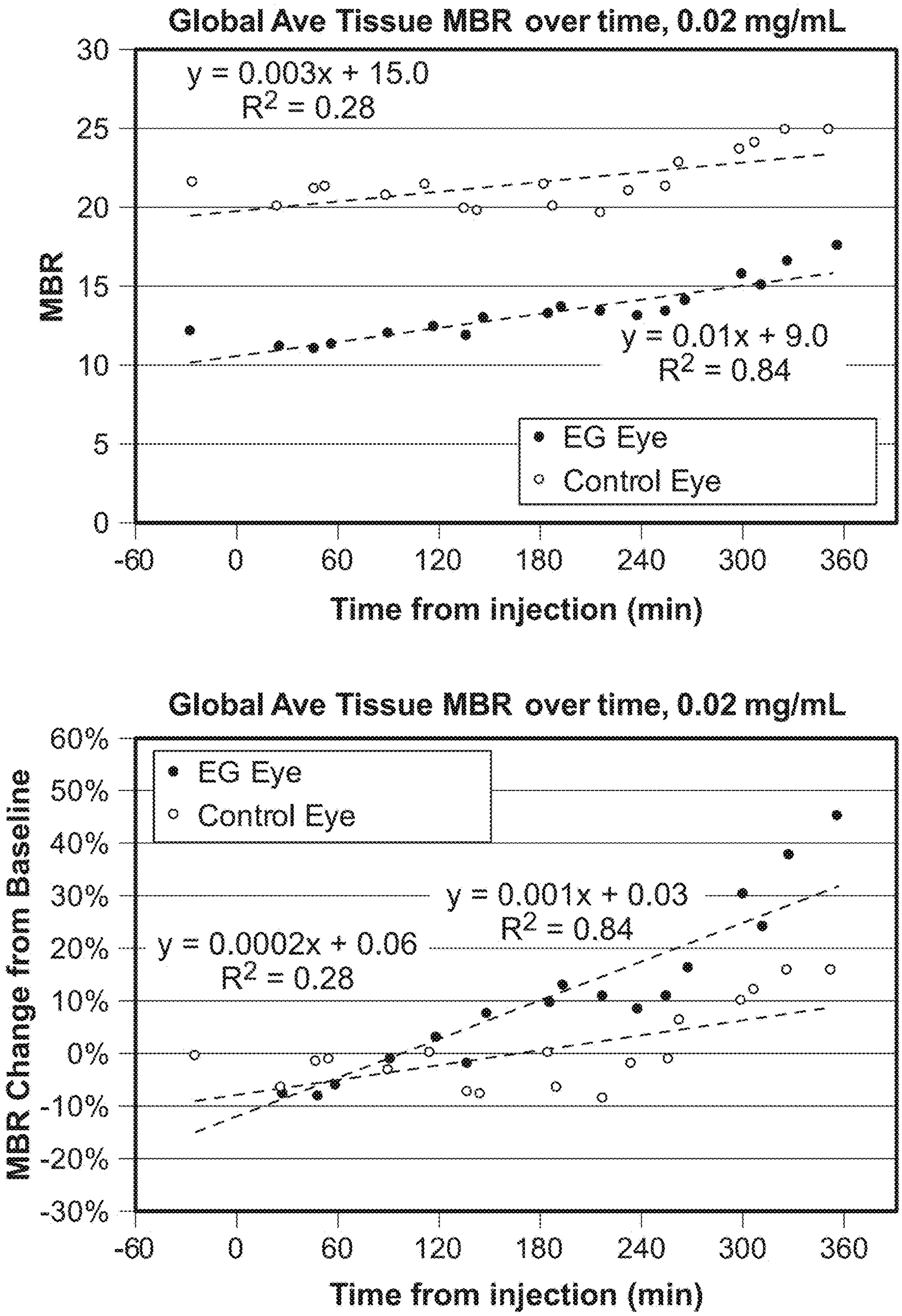
Figure 7K:
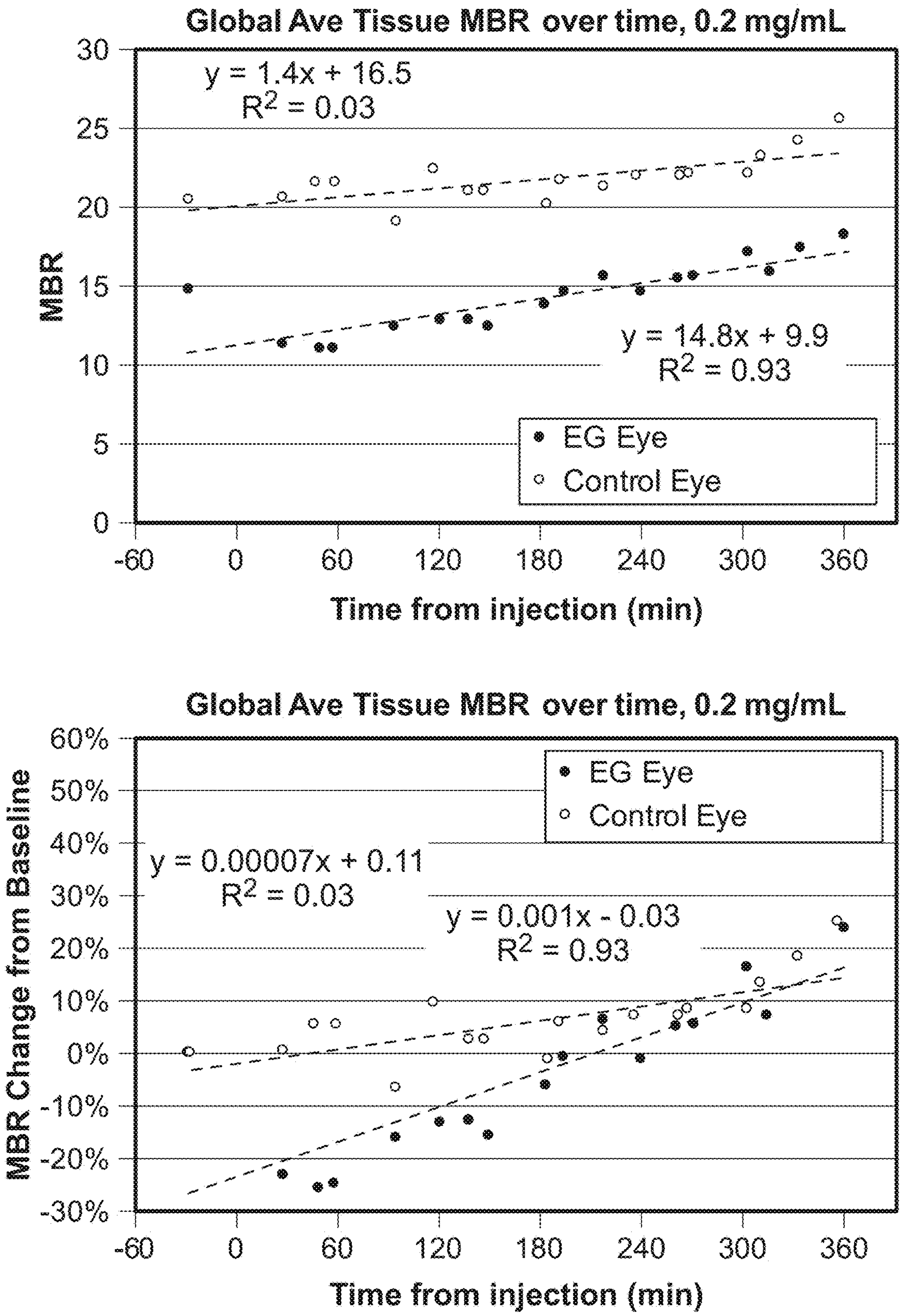
Figure 7L:
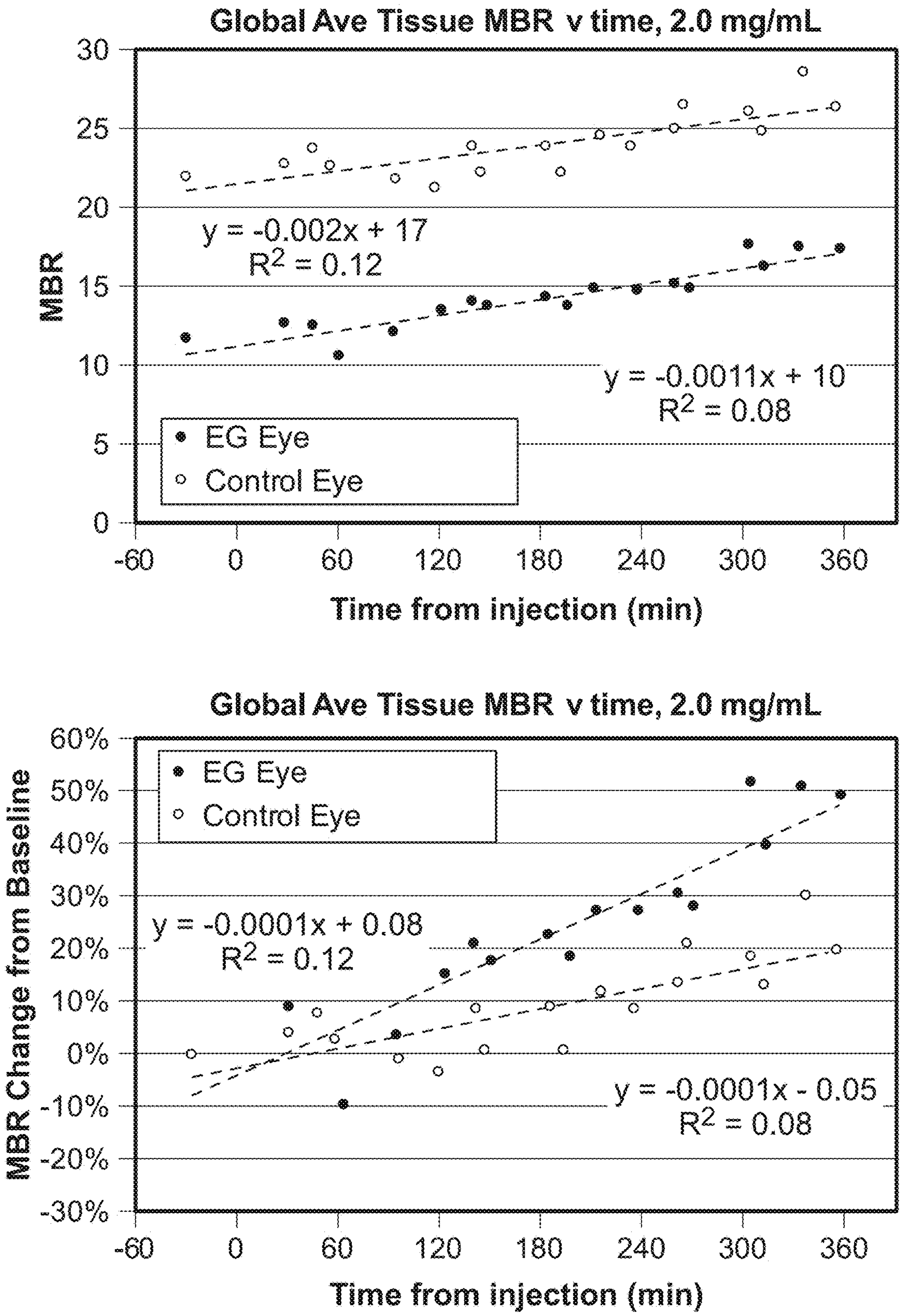
Figure 7M:
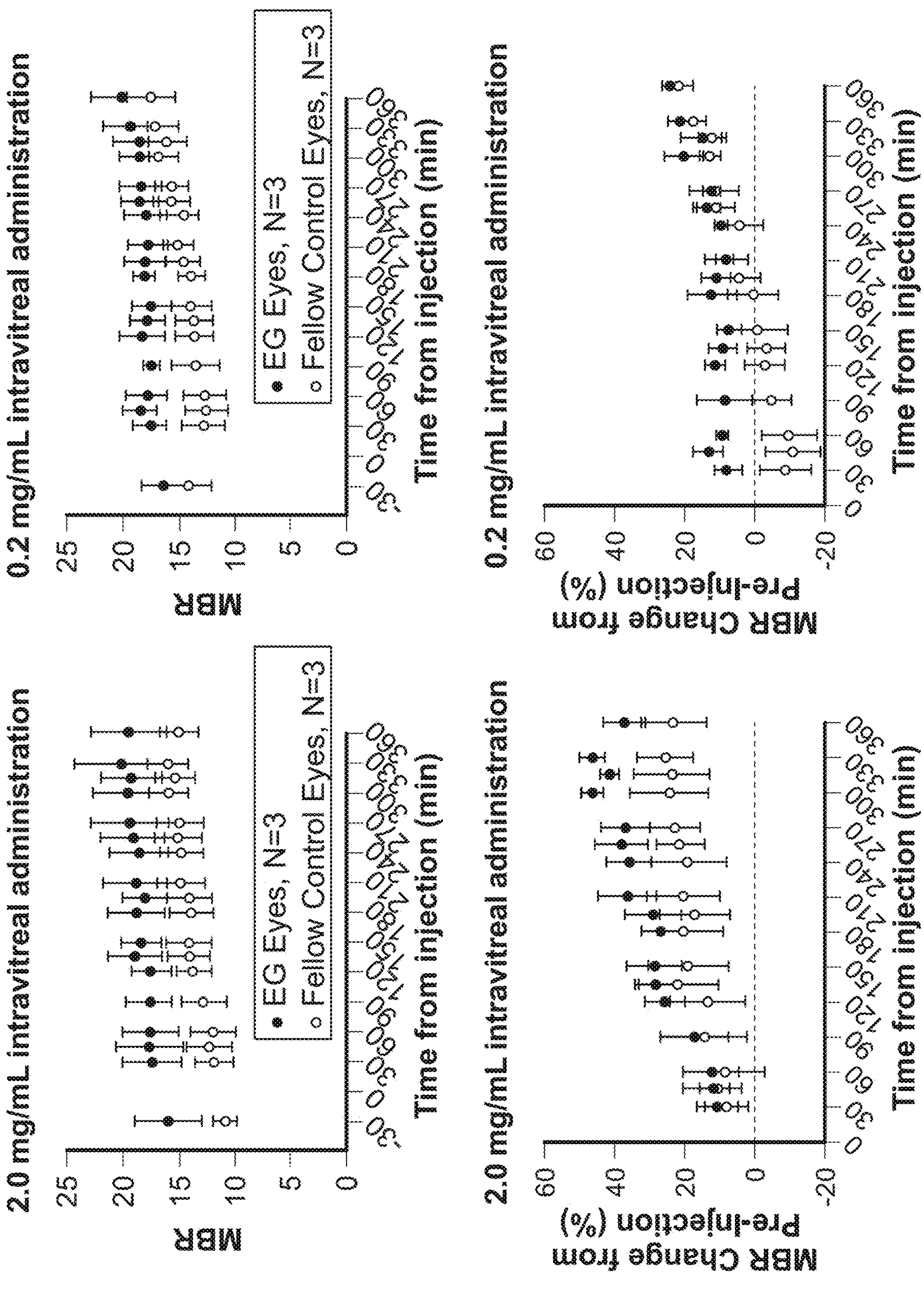
FIG. 7M shows the aggregate results from the three non-human primates.
Figure 7M:
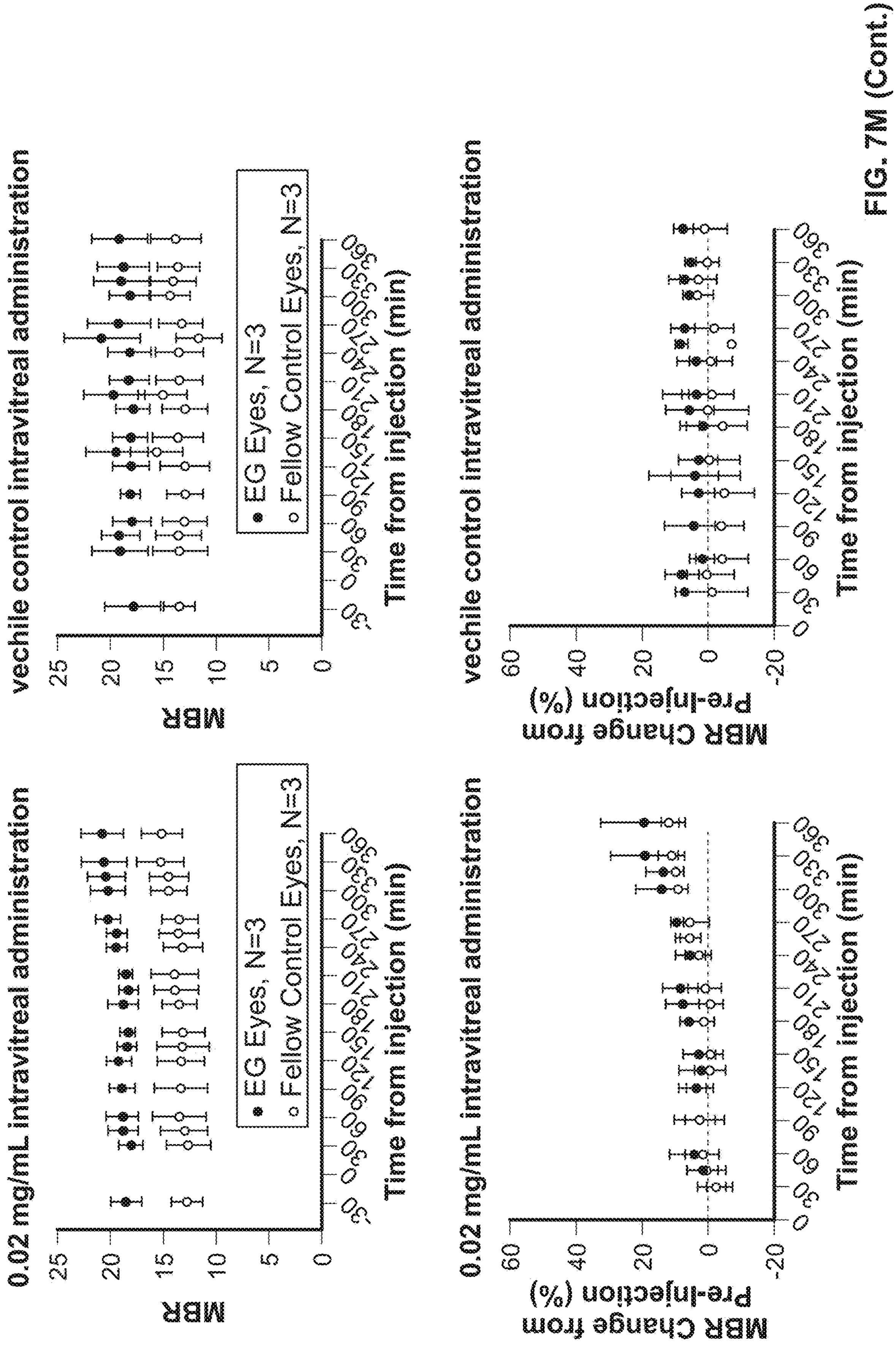

A study was performed to compare an experimental glaucoma eye and a contralateral healthy eye (control) of three non-human primates in global average mean blur rate (MBR) and MBR change from baseline over time as an index of ONH blood flow in a laser-induced glaucoma model. More specifically, a vehicle control, 0.02 mg/mL of Edonentan, 0.2 mg/mL of Edonentan, or 2.0 mg/mL of Edonentan was intravitreally administered (50 μL) to a glaucomatous eye of each of three non-human primates (rhesus macaque, *Macaca mulatta*). The ONH blood flow was then measured over 6 hours using laser speckle flowgraphy (LSFG), as shown in FIGS. 7A-7L. These graphs show the ONH blood flow in the three non-human primates after IVT administration of a vehicle alone (FIG. 7A, FIG. 7E, and FIG. 7I), 0.02 mg/mL of Edonentan (FIG. 7B, FIG. 7F, and FIG. 7J), 0.2 mg/mL of Edonentan (FIG. 7C, FIG. 7G, and FIG. 7K) or 2.0 mg/mL of Edonentan (FIG. 7D, FIG. 7H, and FIG. 7L). FIGS. 7A-7L reveal the improvement of ONH blood flow in a dose-dependent manner after treatment with Edonentan. The aggregate results from the three non-human primates are shown in FIG. 7M, which show that Edonentan clearly exhibits does-related increase of ONH blood flow, resulting from dilation of retinal arteries, veins, and capillaries in experimental glaucoma eyes, as compared to control eyes.

Figure 7N:
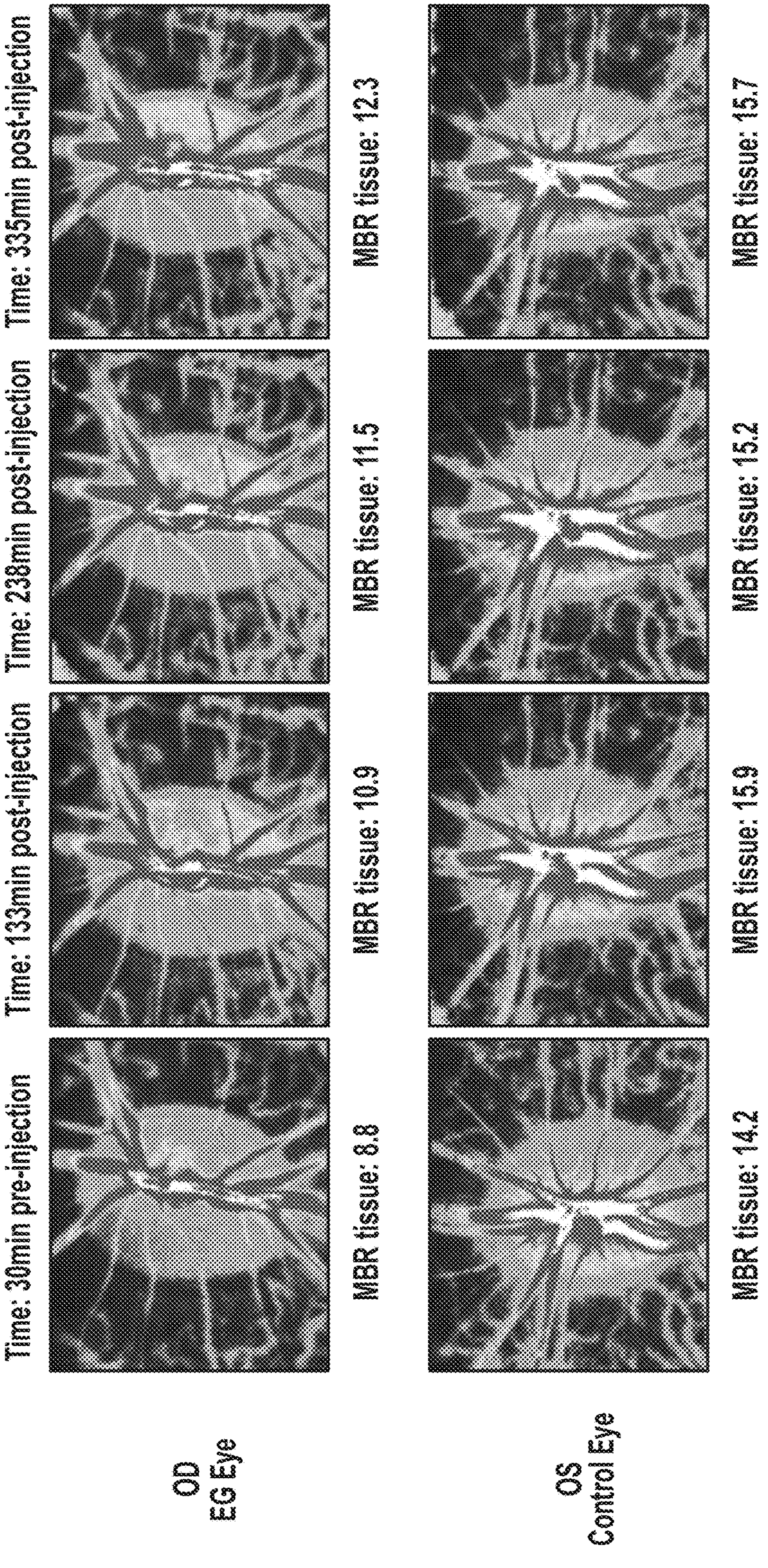
FIG. 7N shows an LSFG scan of one of the non-human primates at various selected time points.

In one of the above three non-human primates, an LSFG scan was performed at various selected time points when Edonentan was administered at 2.0 mg/mL. The results are shown in FIG. 7N.

Effect of Edonentan on Intraocular Pressure after Topical Administration

A single dose of 0.5% Timolol or a single dose of 2 mg/mL Edonentan was topically administered to three non-human primates that have laser-induced glaucoma in their right eyes (OD) with 1-week wash-out in a randomized order.

Study Results:

Control 1: A single dose of 50 μL of topical Timolol 0.5% in each eye showed an IOP reduction of about 20% from pre-dose to post-dose (120 minutes).

Control 2: A single dose of 50 μL of topical Timolol 0.5% in each eye showed an IOP reduction of about 30% from pre-dose to post-dose (120 minutes).

Non-human Primate 1: 50 μL of Edonentan eyedrop (2 mg/mL) in the experimental glaucoma eye showed an IOP reduction of about 60% from pre-dose to post-dose (120 minutes) and in the contralateral healthy eye showed an IOP reduction of about 10% from pre-dose to post-dose (120 minutes).

Non-human Primate 2: 50 μL of Edonentan eyedrop (2 mg/mL) in the experimental glaucoma eye showed an IOP reduction of about 50% from pre-dose to post-dose (15 minutes) and about 30% from pre-dose to post-dose (120 minutes). 50 μL of Edonentan eyedrop (2 mg/mL) in the contralateral healthy eye showed an IOP reduction of about 20% from pre-dose to post-dose (15 minutes) and about 0% from pre-dose to post-dose (120 minutes).

Non-human Primate 3: 50 μL of Edonentan eyedrop (2 mg/mL) in the experimental glaucoma eye showed an IOP reduction of about 40% from pre-dose to post-dose (15 minutes) and about 40% from pre-dose to post-dose (120 minutes). 50 μL of Edonentan eyedrop (2 mg/mL) in the contralateral healthy eye showed an IOP reduction of about 10% from pre-dose to post-dose (15 minutes) and about 40% from pre-dose to post-dose (120 minutes).

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Further, from the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of improving a visual function in a subject diagnosed with glaucoma, wherein the method comprises administering a composition comprising a therapeutically effective amount of edonentan, or a pharmaceutically acceptable salt thereof to an optical tissue of said subject.

2. The method of claim 1, wherein the visual function is selected from the group consisting of peripheral vision, central vision, and contrast sensitivity.

3. The method of claim 1, wherein the administering comprises injecting edonentan to the back of the eye.

4. The method of claim 3, wherein the injecting comprises injecting edonentan to the back of the eye using an intravitreal, suprachoroidal, subretinal, or implant delivery platform.

5. The method of claim 3, wherein the injecting comprises injecting edonentan to the back of the eye using an intravitreal, suprachoroidal, or implant delivery platform with a frequency of every 3 to 12 months.

6. The method of claim 3, wherein the injecting comprises injecting edonentan to the back of the eye using an intravitreal, suprachoroidal, or implant delivery platform with a frequency of every 3 to 6 months.

7. The method of claim 3, wherein the injecting comprises injecting edonentan to the back of the eye using an intravitreal, suprachoroidal, or implant delivery platform with a frequency of every 4 to 6 months.

8. A method of improving a visual function in a subject diagnosed with glaucoma, wherein the method comprises administering a composition comprising about 100 μg and about 500 μg or between about 500 μg to about 4 mg of edonentan, or a pharmaceutically acceptable salt thereof to an optical tissue of said subject.

9. The method of claim 8, wherein the visual function is selected from the group consisting of peripheral vision, central vision, and contrast sensitivity.

10. The method of claim 8, wherein the administering comprises injecting edonentan to the back of the eye.

11. The method of claim 10, wherein the injecting comprises injecting edonentan to the back of the eye using an intravitreal, suprachoroidal, subretinal, or implant delivery platform.

12. The method of claim 10, wherein the injecting comprises injecting edonentan to the back of the eye using an intravitreal, suprachoroidal, or implant delivery platform with a frequency of every 3 to 12 months.

13. The method of claim 10, wherein the injecting comprises injecting edonentan to the back of the eye using an intravitreal, suprachoroidal, or implant delivery platform with a frequency of every 3 to 6 months.

14. The method of claim 10, wherein the injecting comprises injecting edonentan to the back of the eye using an intravitreal, suprachoroidal, or implant delivery platform with a frequency of every 4 to 6 months.

15. A method of improving optic nerve head blood flow in a subject diagnosed with glaucoma, wherein the method comprises administering a composition comprising a therapeutically effective amount of edonentan, or a pharmaceutically acceptable salt thereof to an optical tissue of said subject.

16. The method of claim 15, wherein the administering comprises injecting edonentan to the back of the eye.

17. The method of claim 16, wherein the injecting comprises injecting edonentan to the back of the eye using an intravitreal, suprachoroidal, subretinal, or implant delivery platform.

18. The method of claim 16, wherein the injecting comprises injecting edonentan to the back of the eye using an intravitreal, suprachoroidal, or implant delivery platform with a frequency of every 3 to 12 months.

19. The method of claim 16, wherein the injecting comprises injecting edonentan to the back of the eye using an intravitreal, suprachoroidal, or implant delivery platform with a frequency of every 3 to 6 months.

20. The method of claim 16, wherein the injecting comprises injecting edonentan to the back of the eye using an intravitreal, suprachoroidal, or implant delivery platform with a frequency of every 4 to 6 months.

21. A method of reducing the rate of retinal nerve fiber layer thinning in a subject diagnosed with glaucoma, wherein the method comprises administering a composition comprising a therapeutically effective amount of edonentan, or a pharmaceutically acceptable salt thereof, to an optical tissue of said subject.

* * * * *